US005646246A

United States Patent [19]
Pettit et al.

[11] Patent Number: 5,646,246
[45] Date of Patent: Jul. 8, 1997

[54] ISOLATION AND STRUCTURAL ELUCIDATION OF THE HUMAN CANCER CELL GROWTH INHIBITORY CYCLIC PEPTIDES PHAKELLISTATIN 4, 5, 6, 7, 8 AND 9

[75] Inventors: George R. Pettit, Paradise Valley; Junping Xu, Tempe, both of Ariz.

[73] Assignee: Arizona Board of Regents acting on behalf of Arizona State University, Tempe, Ariz.

[21] Appl. No.: 338,383

[22] Filed: Nov. 14, 1994

[51] Int. Cl.⁶ .................................. C07K 5/12; C07K 7/64
[52] U.S. Cl. ........................ 530/321; 530/317; 530/328; 530/329
[58] Field of Search ................................ 514/9, 11, 15, 514/16; 530/317, 321, 328, 329

[56] References Cited

PUBLICATIONS

Pettit et al., "Isolation of Doastatins 10–15 from the marine mollusc Dolabella Auricularia," Tetrahedron, vol. 49, No. 41, pp. 9151–9170. 1993.

Pettit et al., "Isolation and Structure of the Marine Sponge Cell Growth Inhibitory Cyclic Peptide Phakellistatin 1," Journal of Natural Products, vol. 56, No. 2, pp. 260–267. Feb. 1993.

*Primary Examiner*—Elizabeth C. Weimar
*Assistant Examiner*—Anish Gupta
*Attorney, Agent, or Firm*—Richard R. Mybeck

[57] ABSTRACT

The cytostatic, cyclic peptides; phakellistatin 4, phakellistatin 5, phakellistatin 6, phakellistatin 7, phakellistatin 8 and phakellistatin 9 were isolated from the Western Pacific Ocean sponge *Phakellia costata*. Structural determination was accomplished by utilizing high-field, 2D-NMR experiments and confirmed by results of FAB-MS/MS studies. The absolute configurations were deduced by analyzing the acid hydrolysates using chiral gas chromatographic analytical techniques. The new cyclic peptides were found to have significant in vitro P388 $ED_{50}$ values which range between 0.18 µg/ml and 4.1 µg/ml.

14 Claims, No Drawings

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 7 amino acid residues
        ( B ) TYPE: amino acid
        ( C ) TOPOLOGY:Cyclic ( i i ) MOLECULE TYPE:
        ( A ) DESCRIPTION: Cycloheptapeptide phakellistatin 4

( i i i ) HYPOTHETICAL: no ( i v ) ANTI-SENSE: no ( v ) FRAGMENT TYPE: circular ( v i ) ORIGINAL SOURCE:
        ( A ) ORGANISM: Phakellia costata
        ( B ) DEVELOPMENTAL STAGE: Whole organism ( v i i ) FEATURE:
        ( A ) NAME/KEY: Phakellistatin 4
        ( B ) IDENTIFICATION METHOD: by experiment using high
            resolution nuclear magnetic resonance, high
            resolution mass spectral analysis, MS/MS
            technique and chiral gas chromatography
        ( C ) OTHER INFORMATION:Phakellistatin 4 cell growth
            inhibition: P388(ED50 0.32 mcg/ml), OVCAR-3
        ( GI50  0.2 mcg / ml ), KM20L2 (GI50 0.3mcg/ml),
            SK-MEL-5 (GI50 0.2mcg.ml) (mcg=microgram)

( x ) PUBLICATION INFORMATION:
        ( A ) AUTHORS: PETTIT, GEORGE R.,
            XU, JUN- PING,
            CICHACZ, ZBIGNIEW,
            SCHMIDT, JEAN M.,
            DORSAZ, ANN- C.
        ( B ) TITLE: Isolation and Structure of the Human Cancer Cell
            Growth Inhibitory Phakellistatin 4 from the Western
            Pacific Sponge Phakellia Costata
        ( C ) JOURNAL: Heterocycles
        ( D ) VOLUME: 40
        ( F ) PAGES: 501 - 506
        ( G ) DATE: 1995

( i x ) SEQUENCE DESCRIPTION: SEQ ID NO: 1:

```
Pro  Thr  Pro  Phe  Ile  Phe  Ser
 1                    5
```

( 2 ) INFORMATION FOR SEQ ID NO: 2:

( i ) SEQUENCE CHARACTERISTICS:
        ( A ) LENGTH: 7 amino acid residues
        ( B ) TYPE: amino acid
        ( C ) TOPOLOGY:Cyclic ( i i ) MOLECULE TYPE:
        ( A ) DESCRIPTION: Cycloheptapeptide phakellistatin 5

( i i i ) HYPOTHETICAL: no ( i v ) ANTI-SENSE: no ( v ) FRAGMENT TYPE: circular ( v i ) ORIGINAL SOURCE:
        ( A ) ORGANISM: Phakellia costata
        ( B ) DEVELOPMENTAL STAGE: Whole organism ( v i i ) FEATURE:

(A) NAME/KEY: Phakellistatin 5
(B) IDENTIFICATION METHOD: by experiment using high
    resolution nuclear magnetic resonance, high
    resolutionm ass spectral analysis, MS/MS technique
    and chiral gas chromatography
(C) OTHER INFORMATION: Phakellistatin 5 cell growth inhibition
    P388(ED50 0.23 mcg g/ml), U.S. National Cancer
    Institute's disease-oriented in vitro primary screen
    indicated mean panel GI50 values of 3 micromolar (viii) PUBLICATION INFORMATION:
    (A) AUTHORS: PETTIT, GEORGE R.,
        XU, JUN- PING,
        CICHACZ, ZBIGNIEW,
        WILLIAMS, MICHAEL D.
        DORSAZ, ANN- C.,
        BRUNE, DANIEL C.,
        BOYD, MICHAEL R.,
        CERNY, RONALD L.
    (B) TITLE: Isolation and Structure of the Marine Sponge
        Cancer Cell Growth Inhibitor Phakellistatin 5
    (C) JOURNAL: Bioorganic & Medicinal Chemistry Letters
    (D) VOLUME: 4
    (F) PAGES: 2091 - 2096
    (G) DATE: 1994

(ix) SEQUENCE DESCRIPTION: SEQ ID NO: 2:

Pro  Phe  Asn  Ala  Met  Ala  Ile
1                   5

(2) INFORMATION FOR SEQ ID NO:3:

(i) SEQUENCE CHARACTERISTICS:
        (A) LENGTH: 7 amino acid residues
        (B) TYPE: amino acid
        (C) TOPOLOGY: Cyclic (ii) MOLECULE TYPE:
        (A) DESCRIPTION: Cycloheptapeptide phakellistatin 6

(iii) HYPOTHETICAL: no (iv) ANTI-SENSE: no (v) FRAGMENT TYPE: circular (vi) ORIGINAL SOURCE:
        (A) ORGANISM: Phakellia costata
        (B) DEVELOPMENTAL STAGE: Whole organism (vii) FEATURE:
        (A) NAME/KEY: Phakellistatin 6
        (B) IDENTIFICATION METHOD: by experiment using high
            resolution nuclear magnetic resonance, high
            resolution mass spectral analysis, MS/MS
            technique and chiral gas chromatography
        (C) OTHER INFORMATION: Phakellistatin 6 cell growth
            inhibition : P388(ED50 0.2 mcg/ml),
            OVCAR-3(GI50 0.02 mcg/ml), SF-295(GI50 0.04 mcg/ml),
            A498(GI50 0.08 mcg/ml), NCI- H460(GI50 0.02 mcg/ml),
            KM20L2(GI50 0.02 mcg/ml), SF-MEL-5(GI50 0.03 mcg/ml)

(viii) PUBLICATION INFORMATION:
        (A) AUTHORS: PETTIT, GEORGE R.,
            XU, JUN- PING,
            CICHACZ, ZBIGNIEW,
            WILLIAMS, MICHAEL D.,
            CHAPUIS, JEAN-C.,
            CERNY, RONALD L.
        (B) TITLE: Isolation and Structure of Phakellistatin
            6 from a Chuuk Archipelago Marine Sponge
        (C) JOURNAL: Bioorganic & Medicinal Chemistry Letters
        (D) VOLUME: 4
        (F) PAGES: 2677 - 2682
        (G) DATE: 1994

(ix) SEQUENCE DESCRIPTION: SEQ ID NO: 3:

```
Pro Trp Leu Pro Ile Pro Phe
 1               5
```

( 2 ) INFORMATION FOR SEQ ID NO:4:

( i ) SEQUENCE CHARACTERISTICS:
        ( A ) LENGTH: 10 amino acid residues
        ( B ) TYPE: amino acid
        ( C ) TOPOLOGY: Cyclic ( i i ) MOLECULE TYPE:
        ( A ) DESCRIPTION: Cyclodecapeptide phakellistatin 7

( i i i ) HYPOTHETICAL: no ( i v ) ANTI-SENSE: no ( v ) FRAGMENT TYPE: circular ( v i ) ORIGINAL SOURCE:
        ( A ) ORGANISM: Phakellia costata
        ( B ) DEVELOPMENTAL STAGE: Whole organism ( v i i ) FEATURE:
        ( A ) NAME/KEY: Phakellistatin 7
        ( B ) IDENTIFICATION METHOD: by experiment using high
            resolution nuclear magnetic resonance, high resolution
            mass spectral analysis, MS/MS technique and chiral gas
            chromatography
        ( C ) OTHER INFORMATION: Phakellistatin 7 cell growth
            inhibition : P388 (ED50 3.0 mcg/ml)

( v i i i ) SEQUENCE DESCRIPTION: SEQ ID NO: 4:

```
Pro Pro Ile Phe Ala Leu Pro Pro Tyr Ile
 1               5                    10
```

( 2 ) INFORMATION FOR SEQ ID NO:5:

( i ) SEQUENCE CHARACTERISTICS:
        ( A ) LENGTH: 10 amino acid residues
        ( B ) TYPE: amino acid
        ( C ) TOPOLOGY: Cyclic ( i i ) MOLECULE TYPE:
        ( A ) DESCRIPTION: Cyclodecapeptide phakellistatin 8

( i i i ) HYPOTHETICAL: no ( i v ) ANTI-SENSE: no ( v ) FRAGMENT TYPE: circular ( v i ) ORIGINAL SOURCE:
        ( A ) ORGANISM: Phakellia costata
        ( B ) DEVELOPMENTAL STAGE: Whole organism ( v i i ) FEATURE:
        ( A ) NAME/KEY: Phakellistatin 8
        ( B ) IDENTIFICATION METHOD: by experiment using high
            resolution nuclear magnetic resonance, high resolution
            mass spectral analysis, MS/MS technique and chiral gas
            chromatography
        ( C ) OTHER INFORMATION: Phakellistatin 8 cell growth
            inhibition : P388 (ED50 2.9 mcg/ml)

( v i i i ) SEQUENCE DESCRIPTION: SEQ ID NO: 5:

```
Pro Pro Ile Phe Val Leu Pro Pro Tyr Ile
 1               5                    10
```

( 2 ) INFORMATION FOR SEQ ID NO:6:

( i ) SEQUENCE CHARACTERISTICS:
        ( A ) LENGTH: 10 amino acid residues
        ( B ) TYPE: amino acid
        ( C ) TOPOLOGY: Cyclic (i i) MOLECULE TYPE:
   (A) DESCRIPTION: Cyclodecapeptide phakellistatin 9

(i i i) HYPOTHETICAL: no (i v) ANTI-SENSE: no (v) FRAGMENT TYPE: circular (v i) ORIGINAL SOURCE:
   (A) ORGANISM: Phakellia costata
   (B) DEVELOPMENTAL STAGE: Whole organism (v i i) FEATURE:
   (A) NAME/KEY: Phakellistatin 9
   (B) IDENTIFICATION METHOD: by experiment using high resolution nuclear magnetic resonance, high resolution mass spectral analysis, MS/MS technique and chiral gas chromatography
   (C) OTHER INFORMATION: Phakellistatin 9 cell growth inhibition : P388 (ED50 4.1 mcg/ml)

(v i i i) SEQUENCE DESCRIPTION: SEQ ID NO: 6:

```
Pro  Pro  Ile  Phe  Val  Leu  Pro  Pro  Tyr  Val
1              5                        10
```

ISOLATION AND STRUCTURAL ELUCIDATION OF THE HUMAN CANCER CELL GROWTH INHIBITORY CYCLIC PEPTIDES PHAKELLISTATIN 4, 5, 6, 7, 8 AND 9

INTRODUCTION

This invention relates generally to the field of agents which may be useful in the field of chemotherapy. More particularly, this invention relates to the discovery and structural elucidation of new cyclic peptides, which have been shown to be cytostatic in vitro, designated herein as phakellistatin 4, phakellistatin 5, phakellistatin 6, phakellistatin 7, phakellistatin 8, and phakellistatin 9.

In part this research was funded by the Outstanding Investigator Grant CA44344-01A1-05 awarded by the Division of Cancer Treatment, National Cancer Institute, DHHS. The U.S. government may have certain rights to this invention.

BACKGROUND OF THE INVENTION

Ancient marine invertebrate species of the *Phyla Bryozoa, Molluska,* and *Porifera* have been well established in the oceans for over one billion years. Such organisms have undergone trillions of biosynthetic reactions of their evolutionary chemistry to reach their present level of cellular organization, regulation and defense.

For example, marine sponges have changed minimally in their physical appearance over the last 500 million years. This suggests a very effective chemical resistance to evolution in response to changing environmental conditions over that period of time. Recognition of the potential for utilizing this biologically potent marine animal for medicinal purposes was recorded in Egypt about 2,700 B.C. and by 200 B.C. certain sea hare extracts were being used in Greece for their curative effect. This consideration along with the observation that marine animals, e.g., invertebrates and sharks, rarely develop cancer led to the systematic investigation of marine animal and plant anticancer compounds.

By 1968, ample evidence had been obtained, based on the U.S. National Cancer Institute's (NCI) key experimental cancer study systems, that certain marine organisms could provide new and antineoplastic and/or cytotoxic agents useful in chemotherapy and might also lead to compounds which would be effective in the control and/or eradication of viral diseases.

Further, these marine organisms were believed to possess potentially useful drug candidates of unprecedented structure which had eluded discovery by other methods of medicinal chemistry. Fortunately, these expectations have been realized, e.g. the discovery of the bryostatins, dolastatins and cephalostatins, many of which are now in preclinical development or human clinical studies.

Those researchers presently involved in medicinal chemistry know well the time lag between the isolation of a new compound and its introduction to the market. Often this procedure takes several years and may take decades. As a result, industry, in association with the U.S. Government, has developed a system of testing criteria which serves two purposes. One is to eliminate those substances which are shown through testing to be economically counterproductive to pursue. The second, more important purpose serves to identify those compounds which demonstrate a high likelihood of success and therefore warrant the further study and qualification, and attendant expense, necessary to meet the stringent regulatory requirements which control the ultimate market place.

The current cost to develop the necessary data required for lawful marketing of a new drug compound approaches ten million dollars per compound. Economics dictate that such a huge investment be made only when there is a reasonable likelihood that it can be recovered. Absent such a likelihood, there will be no investment and, without investment, the research requisite for the discovery of these potentially life saving compounds will cease.

Current research in the control of cancer in the U.S. is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and is accepted in scientific circles. The protocol, and the established statistical means for analyzing the results obtained by the standardized testing are fully described in the literature. See: Boyd, Dr. Michael R., *Principles & Practice of Oncology*, PPO Updates, Volume 3, Number 10, October 1989, for a general overview of the testing protocol; Monks, Anne et al., "Feasibility of a High-Flux Anticancer Drug Screen Using a Diverse Panel of Cultured Human Tumor Cell Lines", 83 *J. Nat. Cancer Inst.*, No. 11, 757 (1991); and Paull, K. D., "Display and Analysis of Patterns of Differential Activity of Drugs Against Human Tumor Cell Lines; Development of Mean Graph and COMPARE Algorithm", 81 *Journal of the National Cancer Institute Reports*, No. 14, 1088, (1989), for a description of the methods of statistical analysis. Each of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs materially from the compounds which are extracts of marine creatures possessing antineoplastic qualities. The collection and processing of these later compounds from their natural sources ranges from grossly impractical to the utterly impossible. Ignoring the ecological impact, the population of these creatures and the cost of collection and extraction make the process unworkable. Artificial synthesis of the active compounds is the only possible solution.

Therefore, the elucidation of the structure of these antineoplastic compounds is essential. After the structure has been determined, a means of synthesis must be determined. This is often a long and arduous procedure because of the idiosyncratic complexity of these naturally occurring, evolutionary modified compounds. In addition, research is necessary to determine whether any portion of the naturally occurring compound is irrelevant to the desired properties, so that focus can be had on the simplest structure having the perceived properties.

The Constitution of the United States (Art. 1, Sec. 8) authorized Congress to establish the U.S. Patent and Trademark Office (USPTO) to promote scientific progress. In order to obtain patent rights, one must show the utility of the invention. Cancer cell growth in humans often causes pain, suffering, and premature death. The inhibition of human cancerous tumor growth as evidenced by NCI cell line data is utilitarian in that inhibited cell growth relieves these conditions, thereby allowing the human thus afflicted to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive and the means for further research.

The recognition of antineoplastic and tumor inhibiting activity as demonstrated by accepted NCI criteria as "utility" can promote research efforts in the U.S. and is unequivocally essential if those efforts are to obtain even a modest modicum of success. To reject the NCI criteria on any grounds can only result in quashing all further research efforts in the U.S. and leave our people at the mercy of those foreign companies who operate in more foresighted jurisdictions.

BRIEF SUMMARY OF THE INVENTION

From 500 kg of the Western Pacific sponge *Phakellia costata* (recollected in 1987 at −15 m by SCUBA on the North Pass of Pis Island, Chuuk) several trace compounds were removed from the P388 (NCI designation) active methylene chloride soluble fraction. These compounds are designated herein as phakellistatin 4, phakellistatin 5, phakellistatin 6, phakellistatin 7, phakellistatin 8, and phakellistatin 9.

All these compounds demonstrate in vitro P388 $ED_{50}$ values of between 0.18 (phakellistatin 6) and 4.1 (phakellistatin 8) µg/ml. In vitro growth inhibitory activity was also demonstrated against human cancer cell lines by phakellistatin 4, phakellistatin 5, phakellistatin 6, phakellistatin 7, phakellistatin 8 and phakellistatin 9.

Accordingly, the primary object of the subject invention is the disclosure of the new in vitro cytostatic peptides designated phakellistatin 4, phakellistatin 5, phakellistatin 6, phakellistatin 7, phakellistatin 8, and phakellistatin 9.

Still another object of the present invention is the disclosure of the method of elucidation of the new in vitro cytostatic peptides from the sea sponge *Phakellia costata*.

These and still further objects as shall hereinafter appear are readily fulfilled by the present invention in a remarkably unexpected manner as will be readily discerned from the following detailed description of exemplary embodiments thereof.

DESCRIPTION OF THE PREFERRED EMBODIMENT

STATISTICAL DEFINITIONS

The following measures are used to express drug activity by giving the drug dose which reduces cell growth to a specified percentage of growth:

$ED_{50}$(P388) and $GI_{50}$ (HTCL) are the drug doses needed to reduce the percent growth to 50%. There is no mathematical difference between $ED_{50}$ and $GI_{50}$, which are both calculated using the same formula. The only difference is historical usage. TGI, (Total Growth Inhibition), is the drug dose needed to yield zero percent growth, i.e., just as many cells at the end of the experiment as were present in the beginning. Whether just as many cells were killed as were produced (steady state), or no growth occurred (total inhibition), cannot be distinguished.

$LC_{50}$, (Lethal Concentration 50%), is the drug concentration which reduces growth to −50%, i.e., removes half of the cells originally present at the beginning of the experiment.

Each drug is tested at five (5) doses: 100—10—1—0.1—0.01 µg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at −50% growth for the $LC_{50}$.

PERCENT OF GROWTH

At the start of an experiment, cells from the in vitro cell cultures are inoculated into the appropriate tubes or microtiter plates. One set of control tubes/plates is immediately counted to determine the number of cells at the start of the experiment. This is the "baseline count", or "$T_{zero}$ reading". At the end of the experiment (48 hours later), a second set of control tubes/plates is analyzed to determine the "Control Growth" value. The growth (or death) of cells relative to the initial quantity of cells is used to define the "Percent of Growth".

| | EXAMPLE: |
|---|---|
| | Baseline Count = 20 |
| | Control Count = 200 |
| | (10-Fold Growth) |
| 100% Growth = Control Growth | 100% Growth = 200 |
| 50% Growth = $T_{zero}$ + $\frac{Control - T_{zero}}{2}$ | 50% Growth = 110 |
| 0% Growth = $T_{zero}$ | 0% Growth = 20 |
| −50% Growth = $T_{zero}/2$ | −50% Growth = 10 |

The in vitro test values for the disclosed compounds are as follows:

TABLE A

ED$_{50}$ for Phakellistatins 4-9 μg/ml

| | 4 | 5 | 6 | 7 | 8 | 9 |
|---|---|---|---|---|---|---|
| | 0.23 | 0.23 | 0.18 | 3.0 | 4.1 | 1.7 |

National Cancer Institute Developmental Therapeutics Program
Mean Graphs

| Phakellistatin | Phakellistatin 4 | Cell Type Leukemia | Cell Line P388 | NSC: V Report Date: September 17, 1993 | Units: Molar | SSPL: r High Conc: 1.000E-05 | Exp. ID: Averaged |

| Panel/Cell Line | Log$_{10}$GI50 | GI50 | Log$_{10}$TGI | TGI | Log$_{10}$LC50 | LC50 |
|---|---|---|---|---|---|---|
| Leukemia | | | | | | |
| CCRF-CEM | -6.43 | | -5.08 | | -5.00 | |
| HL-60(TB) | -6.82 | | -5.59 | | -5.00 | |
| K-562 | -6.41 | | -5.00 | | -5.00 | |
| MOLT-4 | -6.28 | | -5.00 | | -5.00 | |
| RPMI-8226 | -6.55 | | -5.00 | | -5.00 | |
| SR | -7.09 | | -5.00 | | -5.00 | |
| Non-Small Cell Lung Cancer | | | | | | |
| A549/ATCC | -5.72 | | -5.00 | | -5.00 | |
| EKVX | -5.70 | | -5.00 | | -5.00 | |
| HOP-62 | -6.28 | | -5.01 | | -5.00 | |
| HOP-92 | -6.24 | | -5.00 | | -5.00 | |
| NCI-H226 | -5.80 | | -5.28 | | -5.00 | |
| NCI-H23 | -6.72 | | -5.24 | | -5.11 | |
| NCI-H322M | -5.89 | | -5.00 | | -5.00 | |
| NCI-H460 | -6.48 | | -5.54 | | -5.00 | |
| NCI-H522 | -6.47 | | -5.49 | | -5.00 | |
| Colon Cancer | | | | | | |
| COLO 205 | -6.64 | | -5.89 | | -5.33 | |
| HCC-2998 | -6.04 | | -5.42 | | -5.00 | |
| HCT-116 | -6.49 | | -5.00 | | -5.00 | |
| HCT-15 | -5.60 | | -5.00 | | -5.00 | |
| HT29 | -6.41 | | -5.35 | | -5.00 | |
| KM12 | -6.43 | | -5.00 | | -5.00 | |
| SW-620 | -6.43 | | -5.00 | | -5.00 | |
| CNS Cancer | | | | | | |
| SF-268 | -6.26 | | -5.00 | | -5.00 | |
| SF-295 | -6.46 | | -5.41 | | -5.00 | |
| SF-539 | -6.68 | | -6.17 | | -5.15 | |
| SNB-19 | -6.04 | | -5.26 | | -5.00 | |
| SNB-75 | -6.68 | | -5.00 | | -5.00 | |
| U251 | -6.48 | | -5.59 | | -5.01 | |

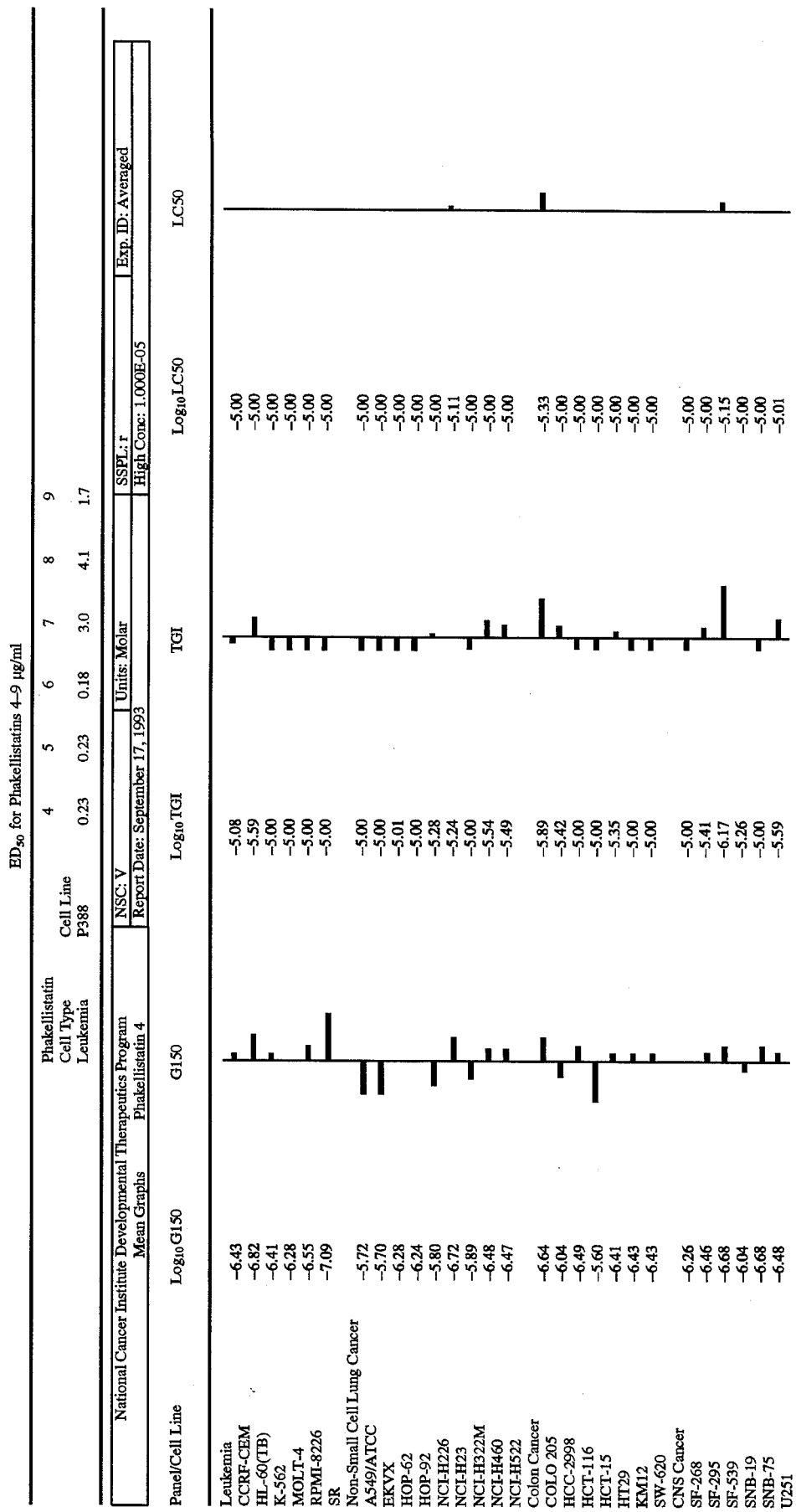

TABLE A-continued

ED$_{50}$ for Phakellistatins 4-9 μg/ml

| | | | |
|---|---|---|---|
| Melanoma | | | |
| LOX-IMVI | −6.20 | | −5.00 |
| MALMB-3M | −6.85 | | −5.00 |
| M14 | −6.34 | | −5.00 |
| SK-MEL-2 | −6.08 | | −5.00 |
| SK-MEL-28 | −6.42 | | −5.00 |
| SK-MEL-5 | −7.03 | −5.37 | −5.00 |
| UACC-257 | −7.14 | −5.39 | −5.19 |
| UACC-62 | −6.64 | −5.00 | −5.00 |
| Ovarian Cancer | | | |
| IGROVI | −6.14 | −5.00 | −5.00 |
| OVCAR-3 | −6.64 | −5.89 | −5.10 |
| OVCAR-4 | −6.52 | −5.24 | −5.12 |
| OVCAR-5 | −5.34 | −5.00 | −5.00 |
| OVCAR-8 | −6.04 | −5.14 | −5.01 |
| SK-OV-3 | −6.24 | −5.00 | −5.00 |
| Renal Cancer | | | |
| 786-0 | −6.25 | −5.00 | −5.00 |
| A498 | −6.48 | −5.70 | −5.10 |
| ACHN | −5.77 | −5.00 | −5.00 |
| CAKI-1 | −5.00 | −5.00 | −5.00 |
| RXF-393 | −5.92 | −5.28 | −5.00 |
| SN12C | −6.10 | −5.00 | −5.00 |
| TK-10 | −5.10 | −5.00 | −5.00 |
| UO-31 | −6.02 | −5.39 | −5.00 |
| Prostate Cancer | | | |
| PC-3 | −6.23 | −5.00 | −5.00 |
| DU-145 | −6.10 | −5.02 | −5.00 |
| Breast Cancer | | | |
| MCF7 | −6.52 | −5.00 | −5.00 |
| MCF7/ADR-RES | −5.04 | −5.00 | −5.00 |
| MDA-MB-231/ATCC | −6.10 | −5.49 | −5.49 |
| HS 578T | −6.55 | −5.42 | −5.00 |
| MDA-MB-435 | −6.89 | −6.43 | −5.47 |
| MDA-N | −7.04 | −6.55 | −5.40 |
| BT-549 | −6.00 | −5.00 | −5.00 |
| T-47D | −5.49 | −5.00 | −5.00 |
| MG_MID | −6.26 | −5.23 | −5.04 |
| Delta | 0.87 | 1.33 | 0.45 |
| Range | 2.14 | 1.55 | 0.49 |

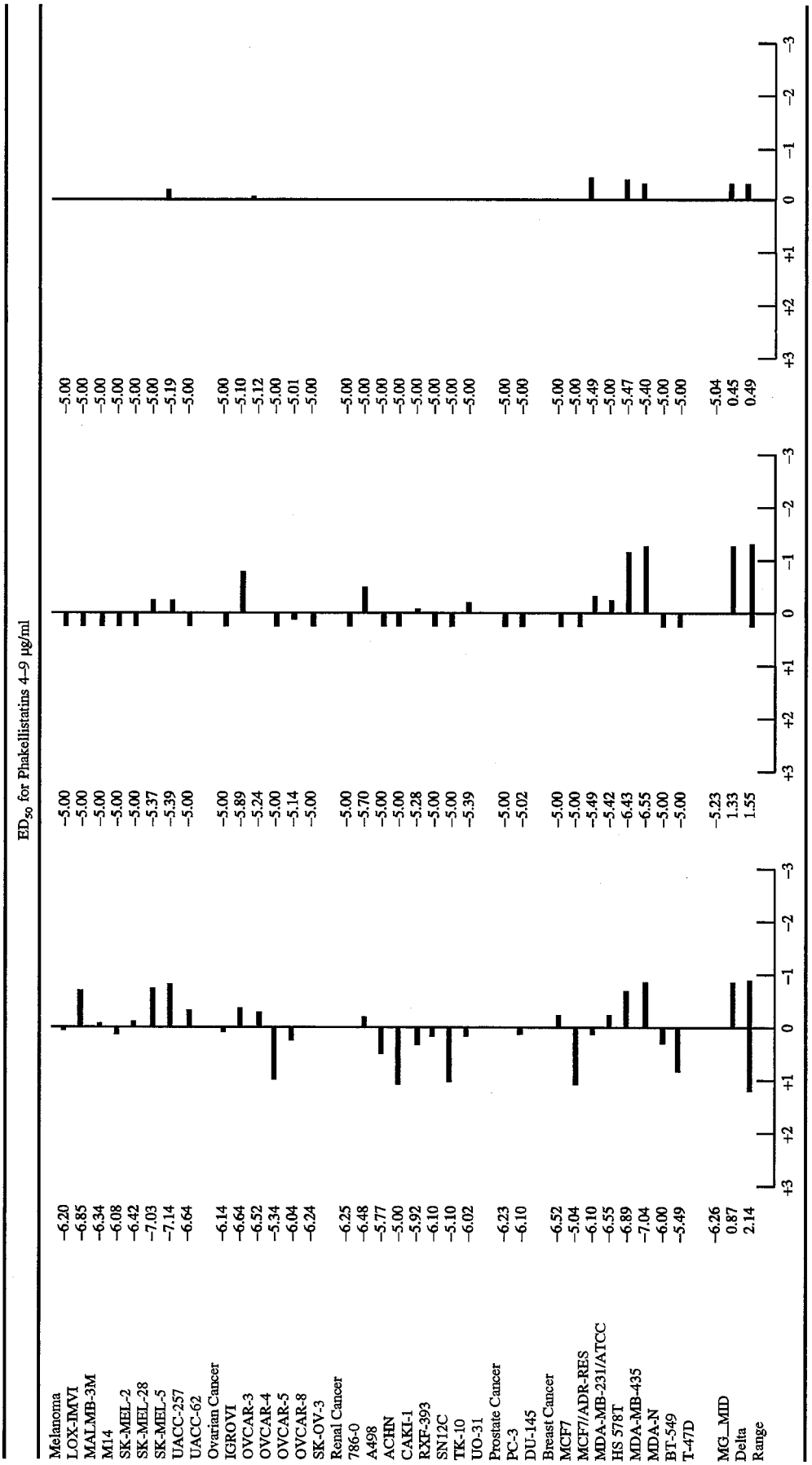

TABLE A-continued

ED$_{50}$ for Phakellistatins 4–9 μg/ml

| | National Cancer Institute Developmental Therapeutics Program Mean Graphs | | Phakellistatin 5 | | NSC: V Report Date: September 17, 1993 | | Units: Molar | | SSPL: r High Conc: 1.000E-05 | | Exp. ID: Averaged |
|---|---|---|---|---|---|---|---|---|---|---|---|
| Panel/Cell Line | Log$_{10}$GI50 | | GI50 | | Log$_{10}$TGI | | TGI | | Log$_{10}$LC50 | | LC50 |
| Leukemia | | | | | | | | | | | |
| CCRF-CEM | −5.64 | | | | −5.06 | | | | −5.00 | | |
| HL-60(TB) | −5.89 | | | | −5.00 | | | | −5.00 | | |
| K-562 | −5.41 | | | | −5.05 | | | | −5.00 | | |
| MOLT-4 | −5.89 | | | | −5.36 | | | | −5.00 | | |
| RPMI-8226 | −6.40 | | | | −5.54 | | | | −5.00 | | |
| SR | −5.64 | | | | −5.09 | | | | −5.00 | | |
| Non-Small Cell Lung Cancer | | | | | | | | | | | |
| A549/ATCC | −5.70 | | | | −5.04 | | | | −5.00 | | |
| EKVX | −5.00 | | | | −5.00 | | | | −5.00 | | |
| HOP-62 | −5.66 | | | | −5.14 | | | | −5.00 | | |
| HOP-92 | −5.77 | | | | −5.09 | | | | −5.00 | | |
| NCI-H226 | −5.57 | | | | −5.00 | | | | −5.00 | | |
| NCI-H23 | −5.38 | | | | −5.00 | | | | −5.00 | | |
| NCI-H322M | −5.00 | | | | −5.00 | | | | −5.00 | | |
| NCI-H460 | −5.66 | | | | −5.07 | | | | −5.00 | | |
| NCI-H522 | −5.36 | | | | −5.00 | | | | −5.00 | | |
| Colon Cancer | | | | | | | | | | | |
| COLO 205 | −5.44 | | | | −5.00 | | | | −5.00 | | |
| HCC-2998 | −5.03 | | | | −5.00 | | | | −5.00 | | |
| HCT-116 | −5.34 | | | | −5.00 | | | | −5.00 | | |
| HCT-15 | −5.00 | | | | −5.00 | | | | −5.00 | | |
| HT29 | −5.19 | | | | −5.00 | | | | −5.00 | | |
| KM12 | −5.19 | | | | −5.00 | | | | −5.00 | | |
| SW-620 | −5.51 | | | | −5.01 | | | | −5.00 | | |
| CNS Cancer | | | | | | | | | | | |
| SF-268 | −5.33 | | | | −5.00 | | | | −5.00 | | |
| SF-295 | −6.42 | | | | −5.82 | | | | −5.19 | | |
| SF-539 | −6.35 | | | | −5.80 | | | | −5.20 | | |
| SNB-19 | −5.52 | | | | −5.00 | | | | −5.00 | | |
| SNB-75 | −6.62 | | | | −5.42 | | | | −5.00 | | |
| U251 | −6.16 | | | | −5.26 | | | | −5.00 | | |

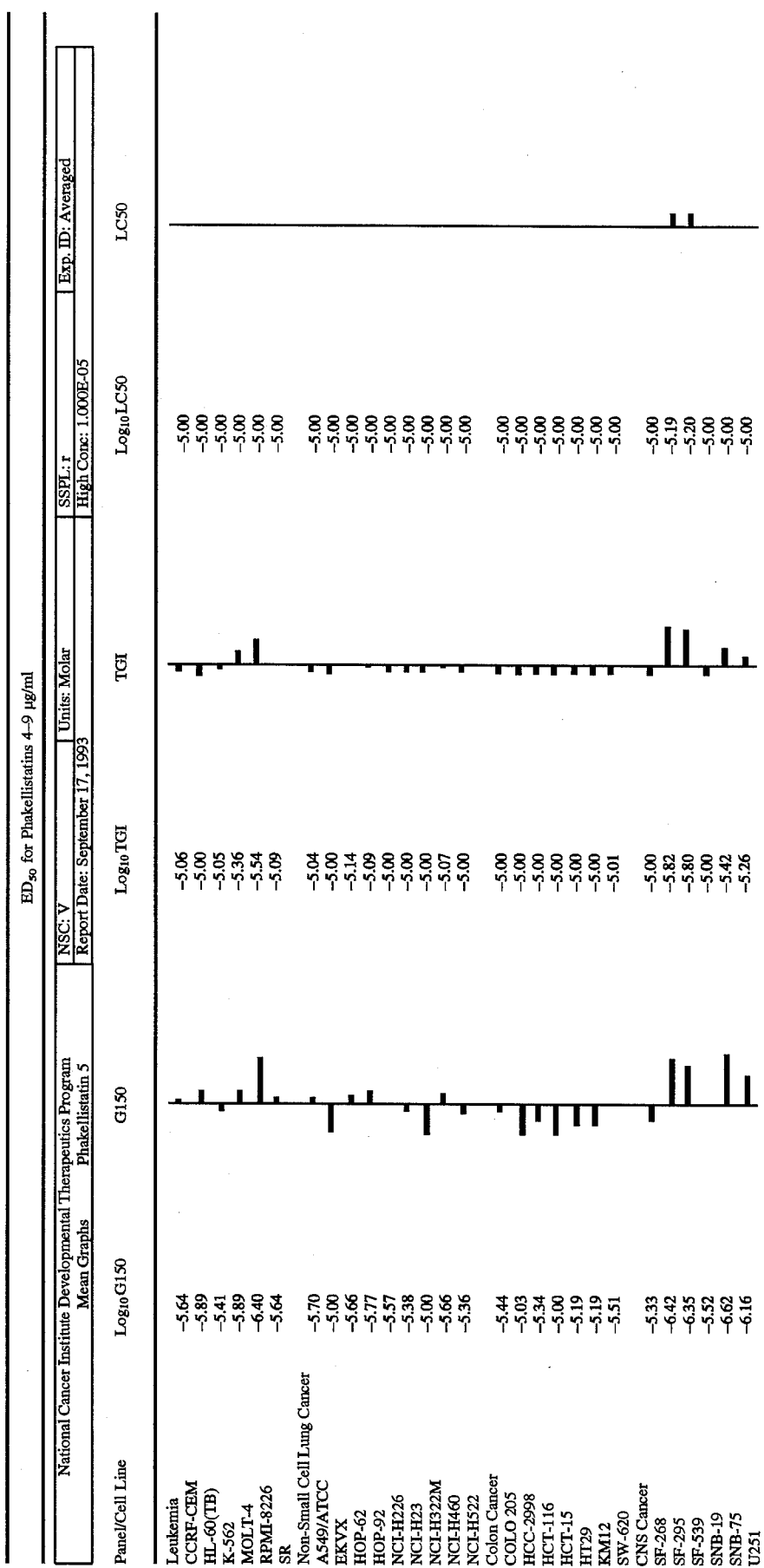

TABLE A-continued

ED$_{50}$ for Phakellistatins 4–9 μg/ml

| | | | |
|---|---|---|---|
| Melanoma | | | |
| LOX-IMVI | −5.47 | −5.06 | −5.00 |
| MALMB-3M | −5.39 | −5.00 | −5.00 |
| M14 | −5.72 | −5.42 | −5.11 |
| SK-MEL-2 | −6.00 | −5.18 | −5.00 |
| SK-MEL-28 | −5.70 | −5.18 | −5.02 |
| SK-MEL-5 | −5.70 | −5.10 | −5.00 |
| UACC-257 | −5.20 | −5.00 | −5.00 |
| UACC-62 | −5.70 | −5.26 | −5.04 |
| Ovarian Cancer | | | |
| IGROVI | −5.29 | −5.00 | −5.00 |
| OVCAR-3 | −5.05 | −5.00 | −5.00 |
| OVCAR-4 | −5.47 | −5.00 | −5.00 |
| OVCAR-5 | −5.24 | −5.00 | −5.00 |
| OVCAR-8 | −5.11 | −5.00 | −5.00 |
| SK-OV-3 | −5.28 | −5.00 | −5.04 |
| Renal Cancer | | | |
| 786-0 | −6.21 | −5.07 | −5.00 |
| A498 | −6.16 | −5.48 | −5.00 |
| ACHN | −5.27 | −5.00 | −5.00 |
| CAKI-1 | −5.00 | −5.00 | −5.00 |
| RXF-393 | −6.04 | −5.46 | −5.07 |
| SN12C | −5.14 | −5.00 | −5.00 |
| TK-10 | −5.09 | −5.00 | −5.00 |
| UO-31 | −5.24 | −5.00 | −5.00 |
| Prostate Cancer | | | |
| PC-3 | −5.66 | −5.28 | −5.25 |
| DU-145 | −5.00 | −5.00 | −5.00 |
| Breast Cancer | | | |
| MCF7 | −5.57 | −5.06 | −5.00 |
| MCF7/ADR-RES | −5.09 | −5.00 | −5.00 |
| MDA-MB-231/ATCC | −5.22 | −5.00 | −5.00 |
| HS 578T | −6.74 | −5.82 | −5.00 |
| MDA-MB-435 | −5.64 | −5.20 | −5.03 |
| MDA-N | −5.59 | −5.11 | −5.01 |
| BT-549 | −5.60 | −5.03 | −5.00 |
| T-47D | −5.04 | −5.00 | −5.00 |
| MG_MID | −5.54 | −5.12 | −5.02 |
| Delta | 1.20 | 0.70 | 0.24 |
| Range | 1.74 | 0.82 | 0.25 |

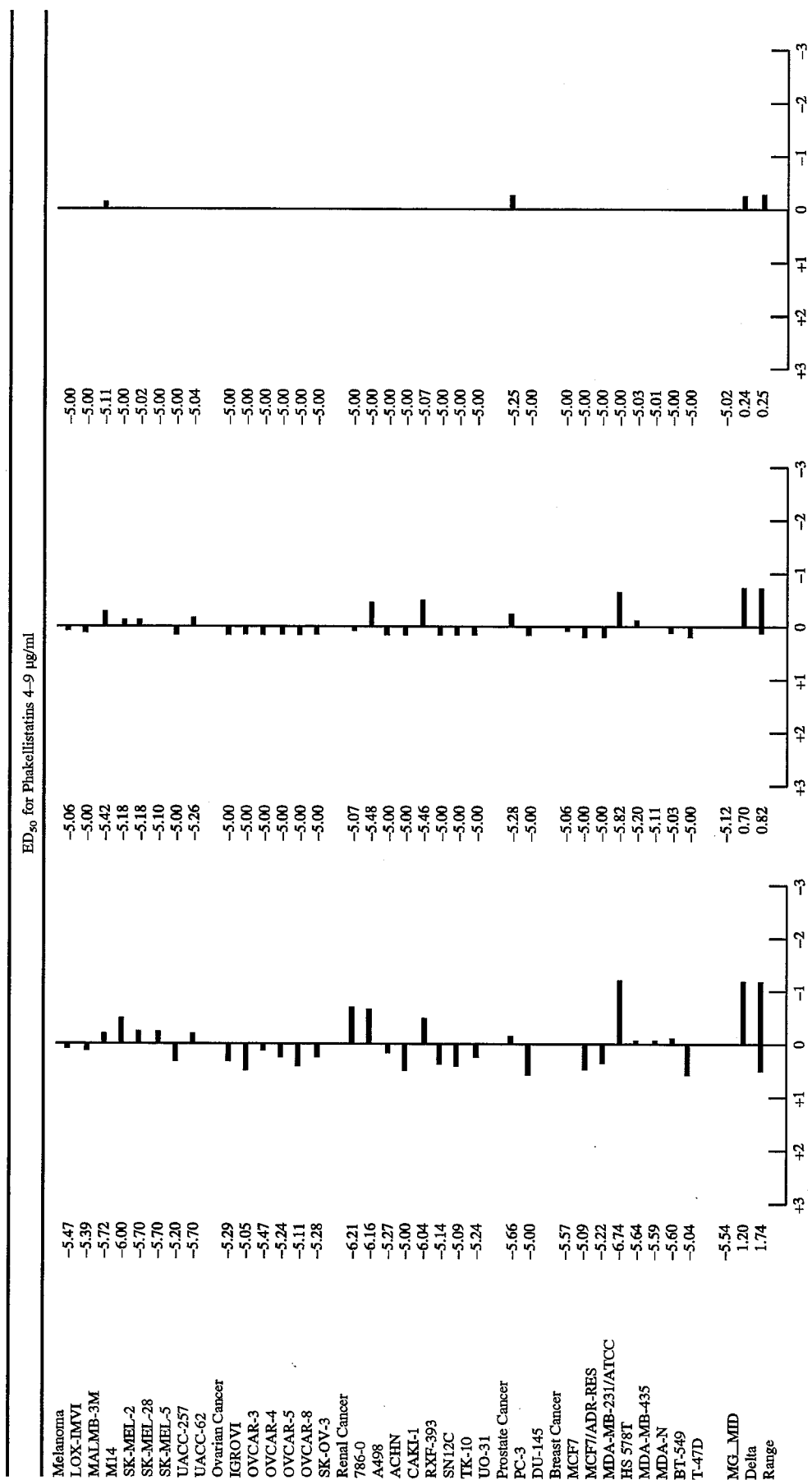

TABLE A-continued

ED$_{50}$ for Phakellistatins 4-9 μg/ml

| | National Cancer Institute Developmental Therapeutics Program Mean Graphs Phakellistatin 7 | | NSC: V 5051 Report Date: August 8, 1994 | Units: Molar | SSPL: r High Conc: −5.0 | Exp. ID: Averaged |
|---|---|---|---|---|---|---|
| Panel/Cell Line | Log$_{10}$GI50 | GI50 | Log$_{10}$TGI | TGI | Log$_{10}$LC50 | LC50 |
| Leukemia | | | | | | |
| CCRF-CEM | −6.41 | | −5.00 | | −5.00 | |
| HL-60(TB) | −6.68 | | −5.36 | | −5.00 | |
| K-562 | −6.51 | | −5.00 | | −5.00 | |
| MOLT-4 | −6.22 | | −5.11 | | −5.00 | |
| RPMI-8226 | −6.04 | | −5.16 | | −5.00 | |
| SR | −6.54 | | −5.00 | | −5.00 | |
| Non-Small Cell Lung Cancer | | | | | | |
| A549/ATCC | −6.06 | | −5.00 | | −5.00 | |
| EKVX | −5.38 | | −5.00 | | −5.00 | |
| HOP-62 | −6.41 | | −5.00 | | −5.00 | |
| HOP-92 | −6.07 | | −5.36 | | −5.00 | |
| NCI-H226 | −5.85 | | −5.19 | | −5.00 | |
| NCI-H23 | −6.21 | | −5.11 | | −5.00 | |
| NCI-H322M | −6.29 | | −5.00 | | −5.00 | |
| NCI-H460 | −6.47 | | −5.00 | | −5.00 | |
| NCI-H522 | −6.59 | | −5.85 | | −5.00 | |
| Colon Cancer | | | | | | |
| COLO 205 | −6.52 | | −5.92 | | −5.13 | |
| HCC-2998 | −6.10 | | −5.21 | | −5.00 | |
| HCT-116 | −6.38 | | −5.00 | | −5.00 | |
| HCT-15 | −5.70 | | −5.00 | | −5.00 | |
| HT29 | −6.47 | | −5.42 | | −5.00 | |
| KM12 | −6.47 | | −5.22 | | −5.00 | |
| SW-620 | −6.44 | | −5.00 | | −5.00 | |
| CNS Cancer | | | | | | |
| SF-268 | −5.60 | | −5.00 | | −5.00 | |
| SF-295 | −6.09 | | −5.35 | | −5.00 | |
| SF-539 | −6.54 | | −5.92 | | −5.20 | |
| SNB-19 | −5.72 | | −5.00 | | −5.00 | |
| SNB-75 | −6.64 | | −5.43 | | −5.00 | |
| U251 | −6.19 | | −5.07 | | −5.00 | |

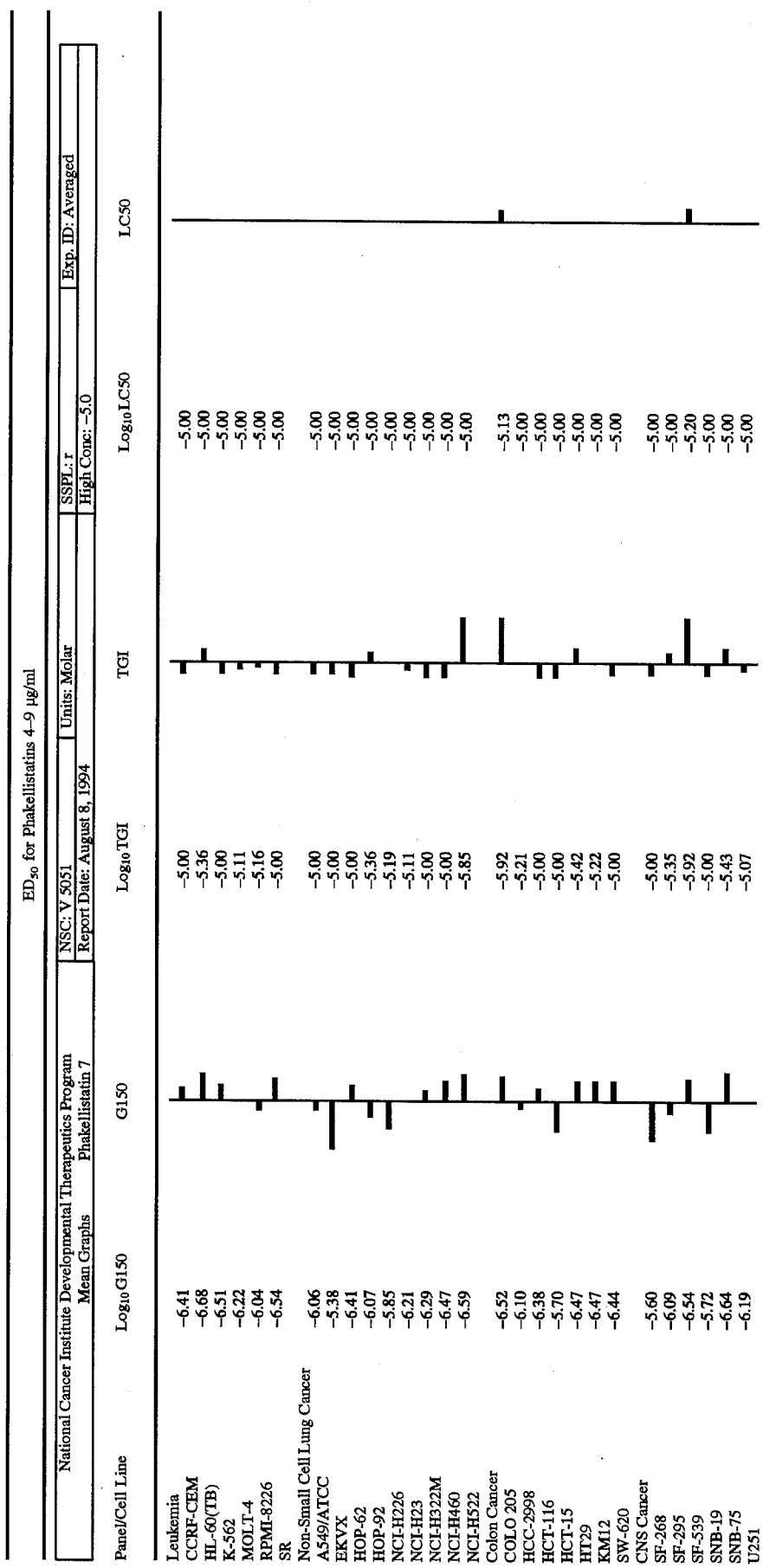

TABLE A-continued

ED$_{50}$ for Phakellistatins 4–9 µg/ml

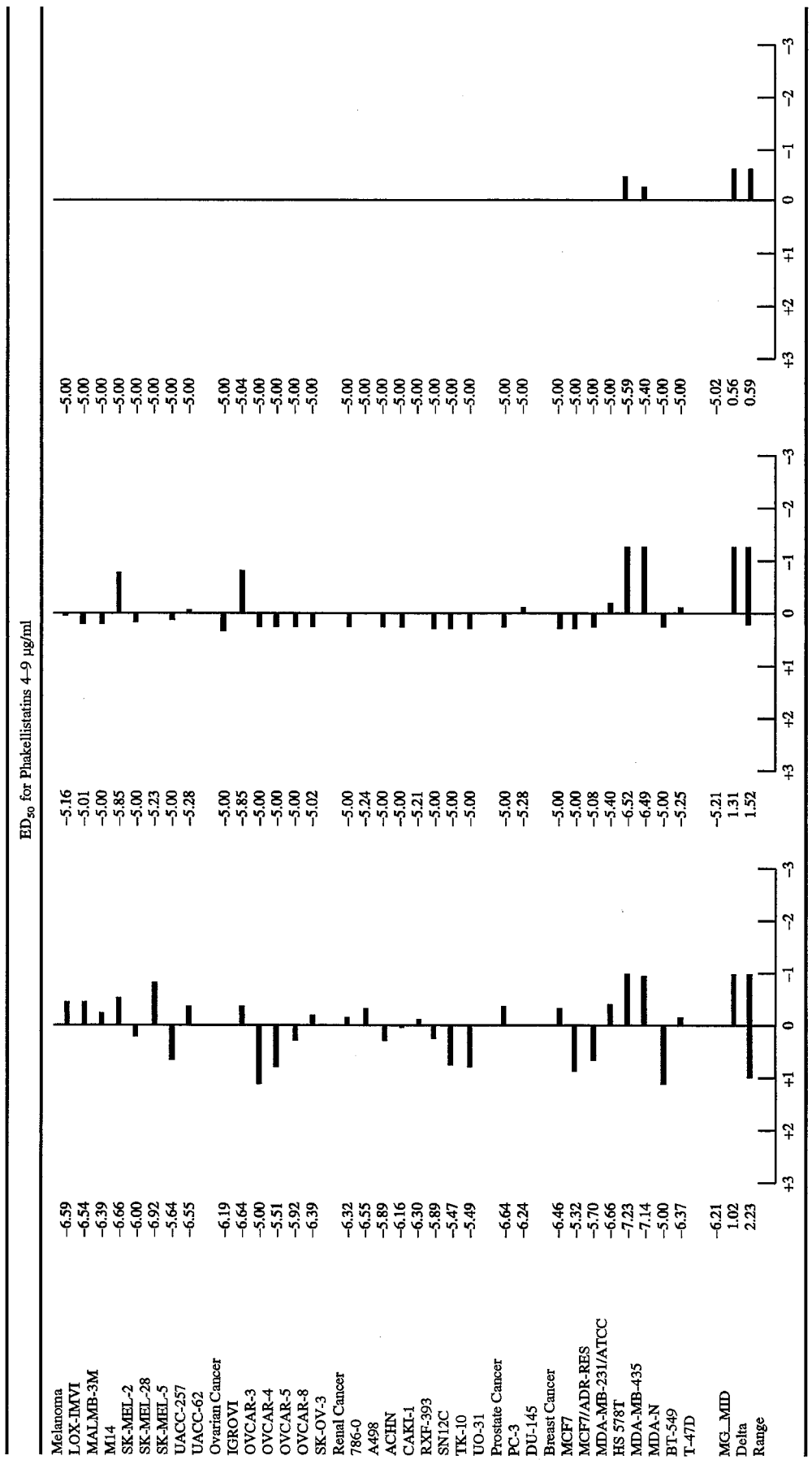

| | | | |
|---|---|---|---|
| Melanoma | | | |
| LOX-IMVI | −6.59 | −5.16 | −5.00 |
| MALMB-3M | −6.54 | −5.01 | −5.00 |
| M14 | −6.39 | −5.00 | −5.00 |
| SK-MEL-2 | −6.66 | −5.85 | −5.00 |
| SK-MEL-28 | −6.00 | −5.00 | −5.00 |
| SK-MEL-5 | −6.92 | −5.23 | −5.00 |
| UACC-257 | −5.64 | −5.00 | −5.00 |
| UACC-62 | −6.55 | −5.28 | −5.00 |
| Ovarian Cancer | | | |
| IGROVI | −6.19 | −5.00 | −5.00 |
| OVCAR-3 | −6.64 | −5.85 | −5.04 |
| OVCAR-4 | −5.00 | −5.00 | −5.00 |
| OVCAR-5 | −5.51 | −5.00 | −5.00 |
| OVCAR-8 | −5.92 | −5.00 | −5.00 |
| SK-OV-3 | −6.39 | −5.02 | −5.00 |
| Renal Cancer | | | |
| 786-0 | −6.32 | −5.00 | −5.00 |
| A498 | −6.55 | −5.24 | −5.00 |
| ACHN | −5.89 | −5.00 | −5.00 |
| CAKI-1 | −6.16 | −5.00 | −5.00 |
| RXF-393 | −6.30 | −5.21 | −5.00 |
| SN12C | −5.89 | −5.00 | −5.00 |
| TK-10 | −5.47 | −5.00 | −5.00 |
| UO-31 | −5.49 | −5.00 | −5.00 |
| Prostate Cancer | | | |
| PC-3 | −6.64 | −5.00 | −5.00 |
| DU-145 | −6.24 | −5.28 | −5.00 |
| Breast Cancer | | | |
| MCF7 | −6.46 | −5.00 | −5.00 |
| MCF7/ADR-RES | −5.32 | −5.00 | −5.00 |
| MDA-MB-231/ATCC | −5.70 | −5.08 | −5.00 |
| HS 578T | −6.66 | −5.40 | −5.00 |
| MDA-MB-435 | −7.23 | −6.52 | −5.59 |
| MDA-N | −7.14 | −6.49 | −5.40 |
| BT-549 | −5.00 | −5.00 | −5.00 |
| T-47D | −6.37 | −5.25 | −5.00 |
| MG_MID | −6.21 | −5.21 | −5.02 |
| Delta | 1.02 | 1.31 | 0.56 |
| Range | 2.23 | 1.52 | 0.59 |

TABLE A-continued

ED$_{50}$ for Phakellistatins 4–9 μg/ml

| National Cancer Institute Developmental Therapeutics Program Mean Graphs Phakellistatin 8 | | NSC: V 5054 Report Date: August 8, 1994 | Units: Molar | SSPL: r High Conc: −5.0 | Exp. ID: Averaged |
|---|---|---|---|---|---|
| Panel/Cell Line | Log$_{10}$GI50 | GI50 | Log$_{10}$TGI | TGI | Log$_{10}$LC50 | LC50 |

| Panel/Cell Line | Log$_{10}$GI50 | Log$_{10}$TGI | Log$_{10}$LC50 |
|---|---|---|---|
| Leukemia | | | |
| CCRF-CEM | −5.18 | −5.00 | −5.00 |
| HL-60(TB) | −5.35 | −5.25 | −5.25 |
| K-562 | −5.24 | −5.00 | −5.00 |
| MOLT-4 | −5.00 | −5.00 | −5.00 |
| RPMI-8226 | −5.00 | −5.00 | −5.00 |
| SR | −5.09 | −5.00 | −5.00 |
| Non-Small Cell Lung Cancer | | | |
| A549/ATCC | −5.00 | −5.00 | −5.00 |
| EKVX | −5.00 | −5.00 | −5.00 |
| HOP-62 | −5.02 | −5.00 | −5.00 |
| HOP-92 | −5.66 | −5.02 | −5.00 |
| NCI-H226 | −5.00 | −5.00 | −5.00 |
| NCI-H23 | −5.00 | −5.00 | −5.00 |
| NCI-H322M | −5.11 | −5.00 | −5.00 |
| NCI-H460 | −5.34 | −5.00 | −5.00 |
| NCI-H522 | −5.48 | −5.03 | −5.00 |
| Colon Cancer | | | |
| COLO 205 | −5.09 | −5.00 | −5.00 |
| HCC-2998 | −5.00 | −5.00 | −5.00 |
| HCT-116 | −5.23 | −5.00 | −5.00 |
| HCT-15 | −5.01 | −5.01 | −5.00 |
| HT29 | −5.28 | −5.00 | −5.00 |
| KM12 | −5.16 | −5.00 | −5.00 |
| SW-620 | −5.40 | −5.00 | −5.00 |
| CNS Cancer | | | |
| SF-268 | −5.00 | −5.00 | −5.00 |
| SF-295 | −5.22 | −5.00 | −5.00 |
| SF-539 | −5.27 | −5.01 | −5.00 |
| SNB-19 | −5.00 | −5.00 | −5.00 |
| SNB-75 | −5.46 | −5.02 | −5.00 |
| U251 | −5.01 | −5.00 | −5.00 |

TABLE A-continued
ED$_{50}$ for Phakellistatins 4–9 µg/ml
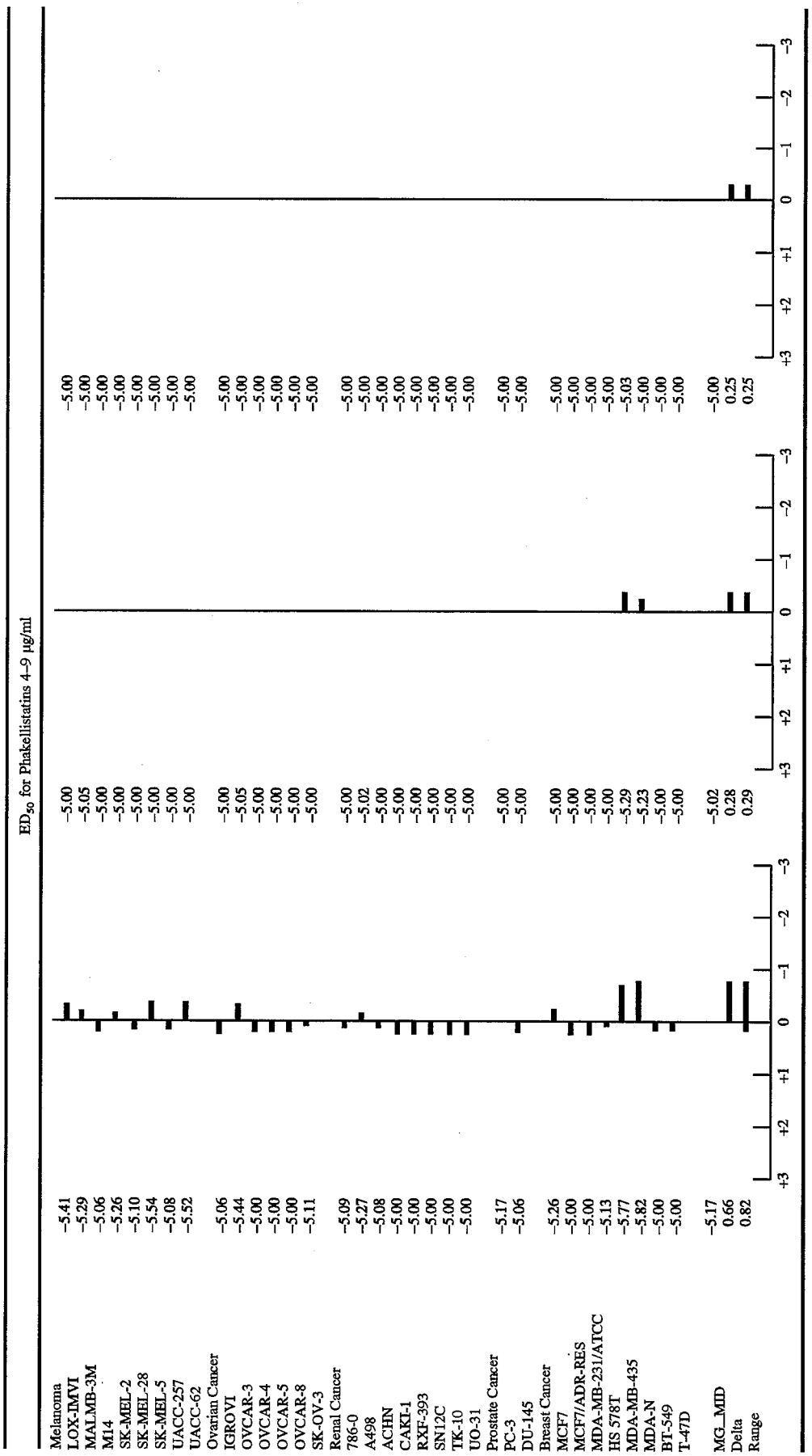
| | | | |
|---|---|---|---|
| Melanoma | | | |
| LOX-IMVI | -5.41 | | |
| MALME-3M | -5.29 | | |
| M14 | -5.06 | | |
| SK-MEL-2 | -5.26 | -5.00 | -5.00 |
| SK-MEL-28 | -5.10 | -5.05 | -5.00 |
| SK-MEL-5 | -5.54 | -5.00 | -5.00 |
| UACC-257 | -5.08 | -5.00 | -5.00 |
| UACC-62 | -5.52 | -5.00 | -5.00 |
| Ovarian Cancer | | -5.00 | -5.00 |
| IGROVI | -5.06 | -5.00 | -5.00 |
| OVCAR-3 | -5.44 | -5.05 | -5.00 |
| OVCAR-4 | -5.00 | -5.00 | -5.00 |
| OVCAR-5 | -5.00 | -5.00 | -5.00 |
| OVCAR-8 | -5.00 | -5.00 | -5.00 |
| SK-OV-3 | -5.11 | -5.00 | -5.00 |
| Renal Cancer | | | |
| 786-0 | -5.09 | -5.00 | -5.00 |
| A498 | -5.27 | -5.02 | -5.00 |
| ACHN | -5.08 | -5.00 | -5.00 |
| CAKI-1 | -5.00 | -5.00 | -5.00 |
| RXF-393 | -5.00 | -5.00 | -5.00 |
| SN12C | -5.00 | -5.00 | -5.00 |
| TK-10 | -5.00 | -5.00 | -5.00 |
| UO-31 | -5.00 | -5.00 | -5.00 |
| Prostate Cancer | | | |
| PC-3 | -5.17 | -5.00 | -5.00 |
| DU-145 | -5.06 | -5.00 | -5.00 |
| Breast Cancer | | | |
| MCF7 | -5.26 | -5.00 | -5.00 |
| MCF7/ADR-RES | -5.00 | -5.00 | -5.00 |
| MDA-MB-231/ATCC | -5.00 | -5.00 | -5.00 |
| HS 578T | -5.13 | -5.00 | -5.00 |
| MDA-MB-435 | -5.77 | -5.29 | -5.03 |
| MDA-N | -5.82 | -5.23 | -5.00 |
| BT-549 | -5.00 | -5.00 | -5.00 |
| T-47D | -5.00 | -5.00 | -5.00 |
| MG_MID | -5.17 | -5.02 | -5.00 |
| Delta | 0.66 | 0.28 | 0.25 |
| Range | 0.82 | 0.29 | 0.25 |

TABLE A-continued

ED₅₀ for Phakellistatins 4–9 μg/ml

| National Cancer Institute Developmental Therapeutics Program Mean Graphs Phakellistatin 9 | | NSC: V 5057 Report Date: August 8, 1994 | | Units: Molar | SSPL: r High Conc: −5.0 | | Exp. ID: Averaged |
|---|---|---|---|---|---|---|---|
| Panel/Cell Line | Log₁₀GI50 | GI50 | Log₁₀TGI | TGI | Log₁₀LC50 | LC50 | |
| Leukemia | | | | | | | |
| CCRF-CEM | −5.22 | | −5.00 | | −5.00 | | |
| HL-60(TB) | −5.39 | | −5.09 | | −5.01 | | |
| K-562 | −5.32 | | −5.00 | | −5.00 | | |
| MOLT-4 | −5.20 | | −5.00 | | −5.00 | | |
| RPMI-8226 | −5.22 | | −5.00 | | −5.00 | | |
| SR | −5.41 | | −5.00 | | −5.00 | | |
| Non-Small Cell Lung Cancer | | | | | | | |
| A549/ATCC | −5.09 | | −5.00 | | −5.00 | | |
| EKVX | −5.06 | | −5.00 | | −5.00 | | |
| HOP-62 | −5.17 | | −5.00 | | −5.00 | | |
| HOP-92 | −5.48 | | −5.00 | | −5.00 | | |
| NCI-H226 | −5.24 | | −5.02 | | −5.00 | | |
| NCI-H23 | −5.27 | | −5.00 | | −5.00 | | |
| NCI-H322M | −5.33 | | −5.00 | | −5.00 | | |
| NCI-H460 | −5.43 | | −5.00 | | −5.00 | | |
| NCI-H522 | −5.62 | | −5.14 | | −5.00 | | |
| Colon Cancer | | | | | | | |
| COLO 205 | −5.54 | | −5.09 | | −5.00 | | |
| HCC-2998 | −5.27 | | −5.00 | | −5.00 | | |
| HCT-116 | −5.37 | | −5.00 | | −5.00 | | |
| HCT-15 | −5.14 | | −5.00 | | −5.00 | | |
| HT29 | −5.48 | | −5.01 | | −5.00 | | |
| KM12 | −5.48 | | −5.01 | | −5.00 | | |
| SW-620 | −5.40 | | −5.00 | | −5.00 | | |
| CNS Cancer | | | | | | | |
| SF-268 | −5.19 | | −5.00 | | −5.00 | | |
| SF-295 | −5.48 | | −5.00 | | −5.00 | | |
| SF-539 | −5.60 | | −5.09 | | −5.00 | | |
| SNB-19 | −5.08 | | −5.00 | | −5.00 | | |
| SNB-75 | −5.54 | | −5.09 | | −5.00 | | |
| U251 | −5.26 | | −5.00 | | −5.00 | | |

TABLE A-continued
ED$_{50}$ for Phakellistatins 4-9 μg/ml
| Cell Line | Value 1 | Value 2 | Value 3 |
|---|---|---|---|
| Melanoma | | | |
| LOX-IMVI | -5.54 | -5.00 | -5.00 |
| MALMB-3M | -5.39 | -5.00 | -5.00 |
| M14 | -5.33 | -5.00 | -5.00 |
| SK-MEL-2 | -5.41 | -5.11 | -5.00 |
| SK-MEL-28 | -5.12 | -5.00 | -5.00 |
| SK-MEL-5 | -5.77 | -5.08 | -5.00 |
| UACC-257 | -5.36 | -5.00 | -5.00 |
| UACC-62 | -5.43 | -5.00 | -5.00 |
| Ovarian Cancer | | | |
| IGROVI | -5.21 | -5.00 | -5.00 |
| OVCAR-3 | -5.48 | -5.12 | -5.00 |
| OVCAR-4 | -5.02 | -5.00 | -5.00 |
| OVCAR-5 | -5.14 | -5.00 | -5.00 |
| OVCAR-8 | -5.10 | -5.00 | -5.00 |
| SK-OV-3 | -5.43 | -5.01 | -5.00 |
| Renal Cancer | | | |
| 786-0 | -5.27 | -5.00 | -5.00 |
| A498 | -5.70 | -5.12 | -5.00 |
| ACHN | -5.17 | -5.00 | -5.00 |
| CAKI-1 | -5.18 | -5.00 | -5.00 |
| RXF-393 | -5.12 | -5.00 | -5.00 |
| SN12C | -5.17 | -5.00 | -5.00 |
| TK-10 | -5.00 | -5.00 | -5.00 |
| UO-31 | -5.00 | -5.00 | -5.00 |
| Prostate Cancer | | | |
| PC-3 | -5.36 | -5.00 | -5.00 |
| DU-145 | -5.17 | -5.00 | -5.00 |
| Breast Cancer | | | |
| MCF7 | -5.68 | -5.25 | -5.25 |
| MCF7/ADR-RES | -5.00 | -5.00 | -5.00 |
| MDA-MB-231/ATCC | -5.00 | -5.00 | -5.00 |
| HS 578T | -5.34 | -5.00 | -5.00 |
| MDA-MB-435 | -5.92 | -5.41 | -5.01 |
| MDA-N | -5.85 | -5.34 | -5.05 |
| BT-549 | -5.35 | -5.00 | -5.00 |
| T-47D | -5.23 | -5.02 | -5.00 |
| MG_MID | -5.33 | -5.03 | -5.01 |
| Delta | 0.60 | 0.38 | 0.25 |
| Range | 0.92 | 0.41 | 0.25 |
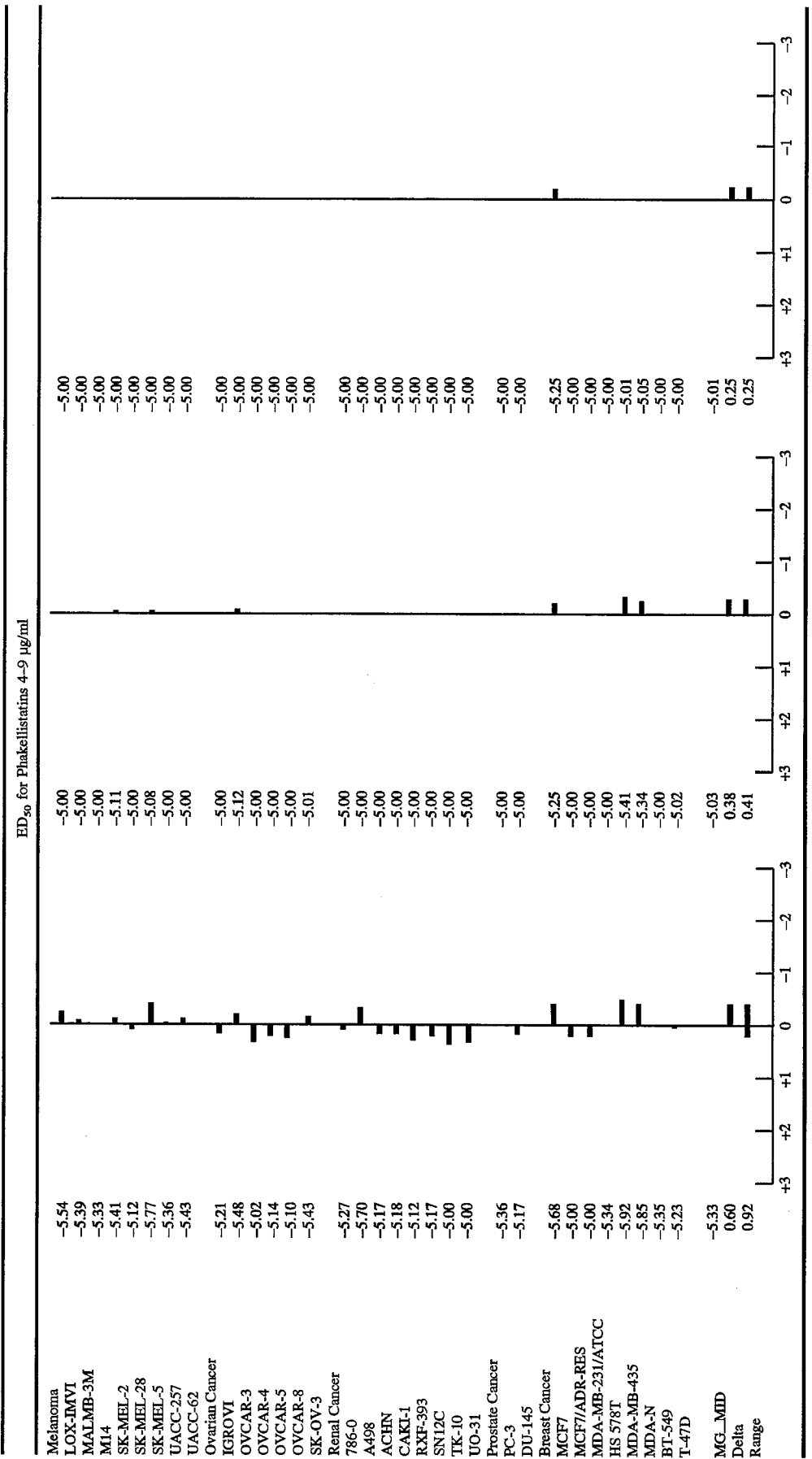

The isolation of the disclosed compounds was accomplished in four groups. Phakellistatin 4 constitutes the first group. Phakellistatin 5 constitutes the second group. Phakellistatin 6 constitutes the third group. The fourth group consists of phakellistatin 7, phakellistatin 8, and phakellistatin 9. Their isolation was accomplished as follows:

A P388 cell line active methylene chloride soluble fraction prepared from 500 kg (wet wt.) of *P. costata* recollected (1987) in Chuuk was separated (murine P388 lymphocytic leukemia bioassay guided) by a series of gel permeation (SEPHADEX LH-20) and partition (LH-20 and SILICA GEL) column chromatographic techniques interspersed by high speed countercurrent-distribution procedures. Final separation was accomplished by HPLC (on C8, with acetonitrile-methanol-water, 10:10:13, as mobile phase) to afford phakellistatins 4–9.

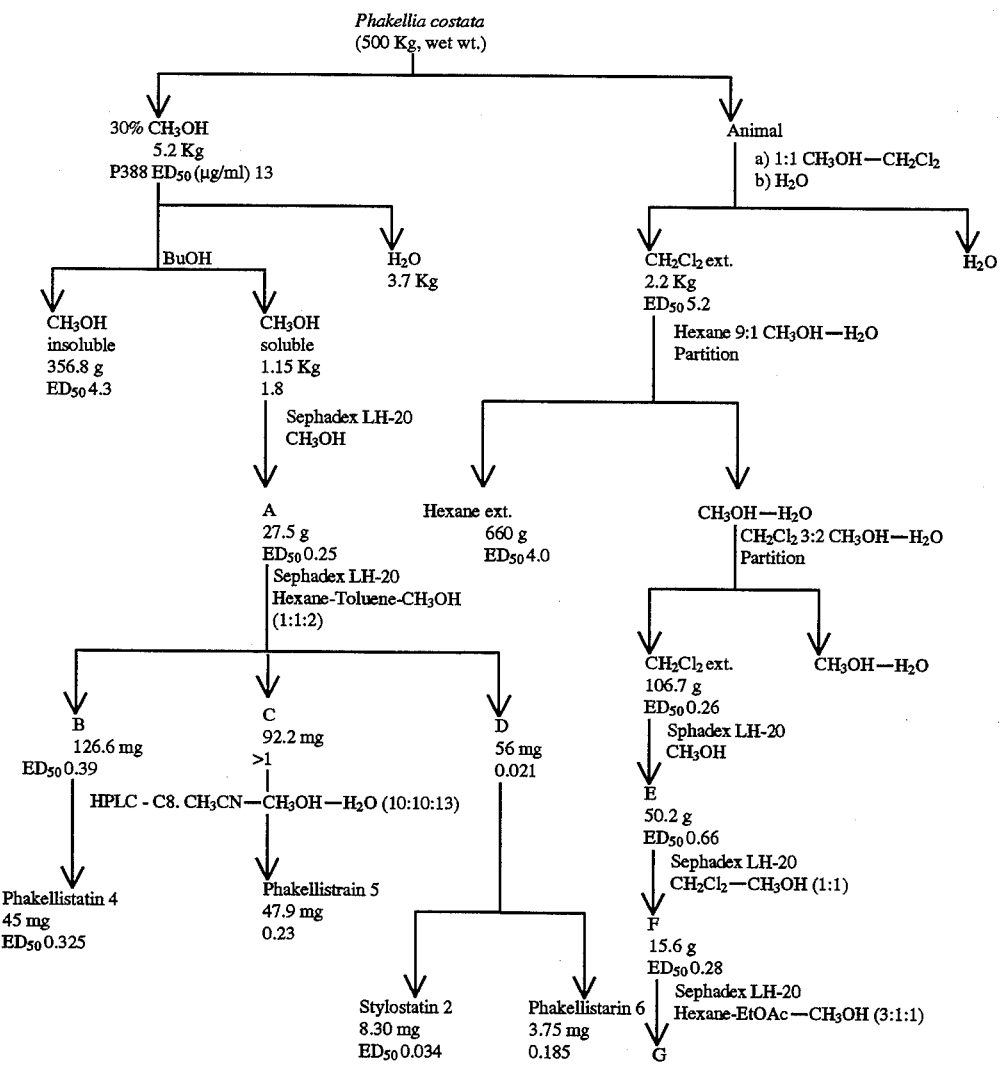

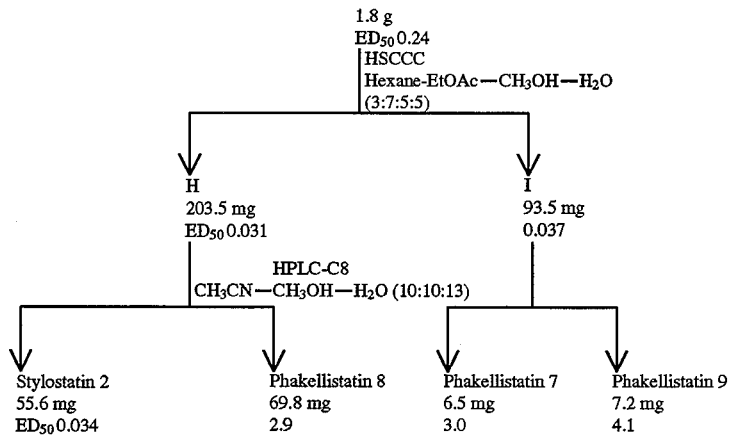

Phakellistatin 4 (1) (45 mg, 9×10⁻⁶% yield, [α]$_D$–97°, c=2.24, CH$_3$OH) was isolated as an amorphous powder (P388, ED$_{50}$ 0.325 μg/ml). Phakellistatin 4 (1) showed a molecular ion peak at m/z 790[M+H]⁺ in the FAB-ms spectrum. The molecular formula was established as $C_{41}H_{56}N_7O_9$ by HRFAB-ms [m/z 790.4146 (M+H)⁺, ΔA+0.6 mmu]. Two groups of ultraviolet absorption maxima appeared at 210–240 nm and 251–267 nm which were attributed to a mono-substituted benzene ring. The 500 MHz and 400 MHz ¹H, ¹³C-NMR and APT spectra gave well separated signals which enabled straightforward interpretation of the COSY spectra. These data together with results of extensive HMQC and HMBC experiments led to the signal assignments and relationships noted in Table 1 for phakellistatin 4 and its assignment as a heptapeptide composed of seven α-amino acid units viz., serine (Ser), isoleucine (Ile), threonine (Thr), proline (Pro ×2) and phenylalanine (Phe ×2).

TABLE 1

The ¹H- and ¹³C-nmr Spectral Data of Phakelliastatin 4 and Their Assignments (in CDCl$_3$)

| | No. | ¹³C ppm | ¹H ppm | J (Hz) | HMBC (¹H to ¹³C) |
|---|---|---|---|---|---|
| Pro-1 | 1 | 170.32 s | | | |
| | 2 | 60.56 d | 4.37 dd | 5.2, 8.4 | 1, 3, 4, 5 |
| | 3 | 29.04 t | 1.62 m | | |
| | | | 2.10 m | | 1, 2, 4 |
| | 4 | 24.63 t | 1.55 m | | |
| | | | 1.82 m | | |
| | 5 | 47.36 t | 3.50 m | | |
| | | | 3.75 m | | |
| Thr | 6 | 170.15 s | | | |
| | 7 | 58.49 d | 4.80 m | 6, 8 | |
| | 8 | 65.82 d | 4.47 m | | 9 |
| | 9 | 19.16 q | 1.35 d | 6.3 | 8 |
| | OH | | 5.32 brd | | |
| | NH | | 8.67 d | 8.7 | 10 |
| Pro-2 | 10 | 171.81 s | | | |
| | 11 | 61.25 d | 5.05 m | | |
| | 12 | 29.28 t | 1.92 m | | 10, 11, 13 |
| | | | 2.58 m | 11.5, 6.4 | 14 |
| | 13 | 22.02 t | 1.70 m | | |
| | | | 2.05 m | | |
| | 14 | 46.18 t | 3.35 m | | 12 |
| | | | 4.00 m | | 12 |
| Ser | 15 | 170.32 s | | | |
| | 16 | 54.37 d | 4.75 m | | |
| | 17 | 61.40 t | 3.55 dd | 8.7, 9.3 | 15, 16 |

TABLE 1-continued

The ¹H- and ¹³C-nmr Spectral Data of Phakelliastatin 4 and Their Assignments (in CDCl$_3$)

| | No. | ¹³C ppm | ¹H ppm | J (Hz) | HMBC (¹H to ¹³C) |
|---|---|---|---|---|---|
| | | | 3.65 m | | 15, 16 |
| | NH | | 8.90 d | 4.6 | 18 |
| Phe-1 | 18 | 173.55 s | | | |
| | 19 | 53.68 d | 4.98 m | | 18, 20, 27 |
| | 20 | 37.95 t | 2.82 t | 10.5 | 19 |
| | | | 3.08 m | | 18, 19, 21, 22 |
| | 21 | 136.43 s | | | |
| | 22 | 129.41 d | 7.25 m | | |
| | 23 | 126.75 d | 7.18 m | | |
| | 24 | 128.37 d | 7.27 m | | |
| | 25 | 126.75 d | 7.18 m | | |
| | 26 | 129.41 d | 7.25 m | | |
| | NH | | 8.55 d | 8.4 | 19, 20, 27 |
| Ile | 27 | 173.50 s | | | |
| | 28 | 66.10 d | 3.12 m | | 27, 29, 30, 32 |
| | 29 | 32.74 d | 2.10 m | | |
| | 30 | 25.23 t | 0.52 m | | |
| | | | 0.92 m | | |
| | 31 | 10.46 q | 0.59 t | 7.0 | 29, 30 |
| | 32 | 14.80 q | 0.15 d | 6.6 | 29, 30 |
| | NH | | 7.60 m | | |
| Phe-2 | 33 | 171.74 s | | | |
| | 34 | 53.40 d | 4.81 m | | 33, 35 |
| | 35 | 37.95 t | 2.92 dd | 8.0, 13.7 | 33, 34, 36, 37 |
| | | | 3.05 m | | 33, 34, 36, 37 |
| | 36 | 136.98 s | | | |
| | 37 | 129.30 d | 7.24 m | | 35 |
| | 38 | 126.56 d | 7.17 m | | |
| | 39 | 128.37 d | 7.27 m | | |
| | 40 | 126.56 d | 7.17 m | | |
| | 41 | 129.30 d | 7.24 m | | 35 |
| | NH | | 7.68 d | 9.2 | 1 |

HMBC and ROE data provided important information about the amino acid sequence in this heptapeptide. Specifically, HMBC correlations from amide NH protons to the amide carbonyl carbon signals such as NH [Thr](σ8.67)/C10[Pro 2](σ 171.81), NH [Ser] (σ 8.90)/C18 [Phe 1](σ 173.55), NH [Phe 1](σ 8.55/C27 [Ile](σ 173.50), NH [Ile](σ 7.60/C33 [Phe 2](σ 171.74) and NH [Phe 2] (σ 7.68/C1 [Pro 1](σ 170.32) were very useful. The ROESY spectrum afforded the following NOE correlations between four amide NH protons and four amino acid α-methine protons, NH [Thr]/H11 [Pro 2] (α 5.05), NH [Ser]/H10 [Phe](σ 4.98), NH [Ile]/H34 [Phe 2] (σ 4.81) and NH [Phe 2]/H2

[Pro 1](G 4.37). Furthermore, another ROE correlation between the amide NH proton of Phe 1 and the β-methine proton of Ile (H29, σ 2.10) was found. That result added more support for the Ile-Phe 1 linkage, and revealed that the amide H–N in Phe 1 to be oriented close to the C–Hβ bond of Ile. The correlations from HMBC and ROESY experiments clearly indicated the sequence of the seven amino acid units as Pro 2-Thr-Pro 1-Phe-Ile-Phe 1-Ser. Although no HMBC or NOE correlations were found between Pro 2 and Ser, the amide nitrogen atom of Pro 2 was assumed to be bonded to the carboxyl carbon of Ser. Because the molecular formula ($C_{41}H_{56}N_7O_9$) indicated phakellistatin (4) to be a cyclic heptapeptide that assumption seemed secure.

Those assumptions were further confirmed by results of amino acid analysis of the phakellistatin 4 acid hydrolysis product. The sequence was further confirmed by results of FAB-MS/MS analysis as are shown below:

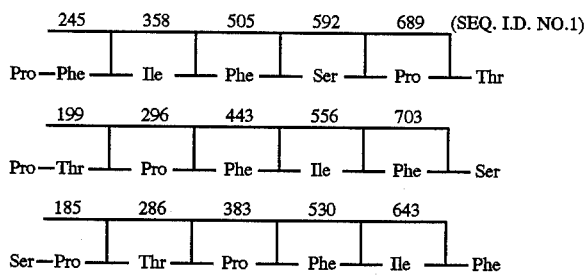

The CAD spectrum of the [M +H]$^+$ ions contained three series of fragment ions (FIG. 1) that define the amino acid unit sequence as cyclo-(Pro-Thr-Pro-Phe-Ile-Phe-Ser) (SEQ. I.D. No. 1). Other ions observed in the CAD spectrum provided additional confirmation for the sequence. The absolute configuration of phakellistatin 4 was ascertained by analyzing the acid hydrolysate converted to N-pentafluoropropionyl isopropyl ester derivatives and using a chiral GC (CHIRASIL-Val III column). By comparing the retention time of each amino acid derivative with those of the authentic S and R amino acids, evidence was obtained that all of the Ser, Ile, Pro and Phe units corresponded to the (S)-configuration while the Thr unit possessed the (R)-configuration. Therefore the structure of phakellistatin 4 was determined to be as shown below:

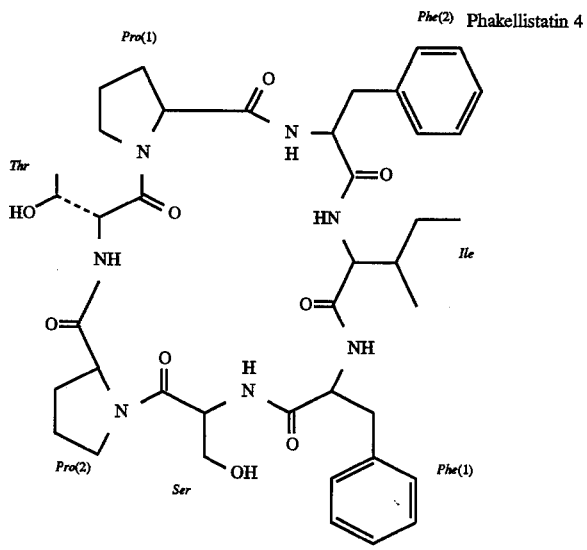

Phakellistatin 4 displayed significant in vitro growth inhibitory activity against murine lymphocytic leukemia P388 (ED$_{50}$ 0.32 µg/ml), and a selection of human cancer cell lines: ovarian (OVACR-3: GI$_{50}$ 0.24 µg/ml), CNS (SF-295: GI$_{50}$ 0.5 µg/ml), renal (A498: GI$_{50}$ 0.81 µg/ml), lung (NCI-H460: GI$_{50}$ 0.34 µg/ml), colon (KM20L2:GI$_{50}$ 0.35 µg/ml) and melanoma (SK-MEL-5:GI$_{50}$ 0.19 µg/ml). When phakellistatin 4 was evaluated (quadruplicate experiments) against the U.S. National Cancer Institute (NCI) human cancer cell line panel a distinctive and reproducible mean graph profile was obtained. The mean panel GI$_{50}$ values were found to be 0.6 µM.

Phakellistatin 5 (2), 47.9 mg, 9.6×10$^{-6}$% yield, [α]$_D$– 102° (c, 2.28 CH$_3$OH) was found to be an amorphous powder (P388:ED$_{50}$ 0.23 µg/ml). The structure of phakellistatin 5 (2) is set forth below:

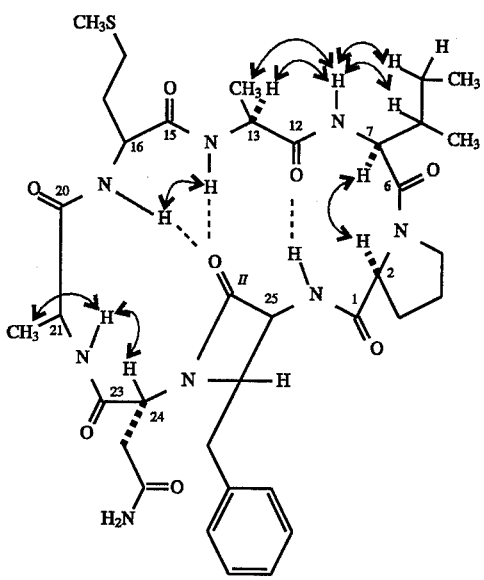

Phakellistatin 5 (2) with NOE ⇔ Correlations

The molecular formula of phakellistatin 5 (2) was determined to be $C_{35}H_{52}N_8O_8S$ by HRFABMS [m/z 745.3706 (M+H)$^+$ for $C_{35}H_{53}N_8O_8S$, Δ-0.1 mmu]. From the molecular formula as well as $^1$H- and $^{13}$C-NMR data, it became evident that phakellistatin 5 was a cyclic peptide. Complete assignments for the $^1$H- and $^{13}$C-NMR resonances (in 3:1 CD$_3$CN–CD$_3$OD, Table 2) were accomplished using a combination of 2D-NMR experiments ($^1$H,$^1$H-COSY, HMQC and HMBC). The detailed NMR studies resulted in identification of seven amino acid units, namely Phe, Ile, Pro, Met, Ala (x2) and Asn. Upon hydrolysis with 6N HCl at 105° C. for 24 hours, five of the same six amino acids and aspartic acid (from Asn) were detected.

The HMBC NMR analyses (Table 2) suggested the seven amino acid sequence presented in structure 2. Two segments, Ile-Ala$^1$-Met-Ala$^2$ and Asn-Phe-Pro were assigned by two-bond $^1$H-$^{13}$C correlations as follows: NH (Ile)/CO (Ala$^1$), NH (Ala$^1$)/CO (Met), NH (Met)/CO (Ala$^2$), NH (Asn)/CO (Phe) and NH (Phe)/CO (Pro). Other useful HMBC correlations were located between αH (Pro)/CO (Pro) and αH (Ala$^2$)/CO (Ala$^2$), and between αH (Pro)/CO (Ile) and αH (Ala$^2$)/CO (Asn). In turn, that clearly identified the (Ile) CO-N (Pro) and (Asn) CO-NH (Ala$^2$) relationships and the cyclic heptapeptide structure (2). Also, cross peaks involving NH (Ile)/αH (Ala$^1$) and NH (Ala$^2$)/αH (Asn) in the ROESY spectrum supported connectivity across the NH (Ile)/CO (Ala$^1$) and NH (Ala$^2$)/CO (Ash) amide bonds. The sequence of amino acid units of cyclic peptide 2 was confirmed by results of FAB-MS/MS studies.

TABLE 2

The $^1$H- and $^{13}$C-NMR Spectral Assignments for Phakellistatin 5 (2) in 3:1 CD$_3$CN—CD$_3$OD

| | No. | $^{13}$C ppm | $^1$H ppm | J (Hz) | HMBC * ($^1$H to $^{13}$C) |
|---|---|---|---|---|---|
| Pro | 1 | 172.34 s | | | |
| | 2 | 62.37 d | 4.42 d | 7.5 | 1, 6 |
| | 3 | 31.91 t | 1.78 m | | 1 |
| | | | 2.23 dd | 12.3, 6.0 | |
| | 4 | 22.29 t | 0.84 m | | |
| | | | 1.61 m | | |
| | 5 | 47.35 t | 2.78 dd | 10.0 | |
| | | | 3.31 m | | |
| Ile | 6 | 173.20 s | | | |
| | 7 | 59.14 d | 4.14 dd | 7.7, 4.1 | 6 |
| | 8 | 37.48 d | 1.74 m | | |
| | 9 | 26.08 t | 1.30 m | | |
| | | | 1.61 m | | |
| | 10 | 11.59 q | 0.86 t | 7.4 | |
| | 11 | 15.76 q | 0.89 d | 7.4 | |
| | NH | | 7.82 brs | | 12 |
| Ala-1 | 12 | 174.32 s | | | |
| | 13 | 49.20 d | 4.54 m | | 12 |
| | 14 | 16.47 q | 1.25 d | 6.5 | |
| | NH | | 7.60 d | 8.0 | 15 |
| Met | 15 | 173.43 s | | | |
| | 16 | 54.35 d | 4.52 m | | |
| | 17 | 32.44 t | 1.98 m | | |
| | | | 2.09 m | | |
| | 18 | 31.61 t | 2.53 m | | 19 |
| | | | 2.45 m | | 19 |
| | 19 | 15.76 q | 2.07 s | | 18 |
| | NH | | 8.12 brs | | 20 |
| Ala-2 | 20 | 175.14 s | | | |
| | 21 | 53.59 d | 3.94 q | 7.4 | 20, 23 |
| | 22 | 17.43 q | 1.38 d | 7.4 | |
| | NH | | 7.69 brs | | |
| Asn | 23 | 172.68 s | | | |
| | 24 | 51.39 d | 4.39 dd | 6.0, 2.8 | |
| | 25 | 37.28 t | 2.94 dd | 15.4, 2.8 | 23, 26 |
| | | | 3.18 m | | |
| | 26 | 174.32 s | | | |
| | NH | | 7.79 d | 4.5 | 23, 27 |
| Phe | 27 | 174.06 s | | | |
| | 28 | 59.60 d | 4.24 m | | 27 |
| | 29 | 38.39 t | 3.15 m | | 28, 30, 31 |
| | | | 3.26 m | | |
| | 30 | 138.94 s | | | |
| | 31 | 130.21 d | 7.23 m | | 32, 33, 34 |
| | 32 | 129.98 d | 7.32 m | | 30, 31, 35 |
| | 33 | 128.17 d | 7.20 m | | |
| | 34 | 129.98 d | 7.32 m | | 30, 31, 35 |
| | 35 | 130.21 d | 7.23 m | | 32, 33, 34 |
| | NH | | 8.53 d | 6.9 | 1 |

* The HMBC spectrum was measured in CD$_3$CN—CD$_3$OH (3:1).

Collisional activation of the [M+H]$^+$ ions of phakellistatin 5 produced immonium ions of Ala (m/z 44), Pro (m/z 70), Leu/Ile (m/z 86), Asn (m/z 87), Met (m/z 104), and Phe (m/z 120). The presence of these amino acids, when combined with the exact mass data, identified the amino acid composition to be 1×Pro, 1×Phe, 1×Asn, 2×Ala, 1×Met, and 1×Leu (Ile). The CAD spectrum of the (M+H)$^+$ ions of phakellistatin 5 shown below contained three series of fragment ions that were used to identify the sequence of amino acid units as cyclo-(Pro-Phe-Asn-Ala-Met-Ala-Ile) (SEQ. I.D. NO. 2).

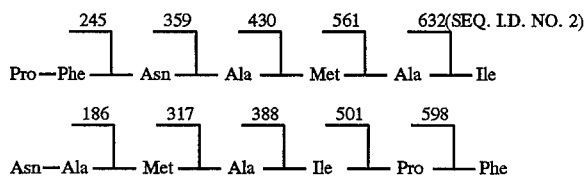

-continued

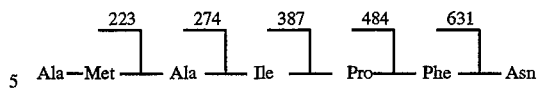

Other ions observed in the CAD spectrum that provided confirmation of the sequence were assigned Ala-Ile (m/z 185), Ile-Pro (m/z 211), Phe-Asn (m/z 262), Phe-Asn-Ala (m/z 333), and Met-Ala-Ile (m/z 316). In summary this allowed the structure of phakellistatin 5 (2) to be assigned cyclo-(Pro-Phe-Asn-Ala-Met-Ala-Ile) (SEQ. I.D. No. 1).

The absolute configuration of phakellistatin 5 (2) was deduced by analyzing an acid hydrolysate converted to N-Pentafluoropropionyl-isopropyl ester derivatives using chiral gas chromatography (CHIRASIL-Val III column). By comparing the retention time of each amino acid derivative with those of the authentic (S)- and (R)- amino acids, it was ascertained that each contained the (S)-configuration except for the (R)-Asp unit. Attention was next directed to a conformational analysis employing high field NMR over the temperature range –25° to 25° C.

The NMR spectra of phakellistatin 5 (2) indicated predominately a single conformer in CD$_3$CN-CD$_3$OH (3:1) solution at ambient temperature. A likely solution conformation of cyclic peptide 2 was deduced from detailed analyses of ROESY and NOESY spectra as a function of temperature dependence of the α-amide proton chemical shifts. The ROESY spectrum showed a cross peak between αH (Pro) and αH (Ile), indicating cis geometry for the amide bond at N (Pro)/CO (Ile). The cis Ile-Pro configuration was supported by the difference (Δδβγ 9.62 ppm) in the Pro β- and γ-carbons $^{13}$C chemical shifts. The Phe, Ala$^1$ and Met α-amide protons showed less temperature dependence (Δδ/Δ$_T$: –2.3, –0.45 and –3.4, respectively) than those of Ile, Asn and Ala$^2$ (Δδ/Δ$_T$: –8.5, –8.0 and –7.4, respectively, suggesting that the three amide protons of Phe, Ala$^1$ and Met participated in intramolecular hydrogen bonds. Also, the NOE correlation between NH (Ala$^1$) and NH (Met) indicated those amide hydrogens were directed inside the peptide ring.

The amide hydrogen chemical shift of Ile showed a large temperature dependence and NOE correlations were observed between NH (Ile)/βH (Ile) and NH (Ile)/βCH$_3$ (Ala$^1$). From this evidence, the Ile amide bond was placed outside the peptide ring. Cross peaks corresponding to NH (Ala$^2$)/αH (Asn) and NH (Ala$^2$)/βCH$_3$ (Ala$^2$) in the ROESY spectrum suggested that the N-H bond of Ala$^2$ was nearly oriented in the same direction as the α-H bond of Asn. In turn, that served to further confirm the (R)-configuration for Asn and suggested that the Asn-Ala$^2$ unit formed a type II'β-turn. turn. Therefore, the backbone of peptide 2 appeared to have one cis amide bond at N(Pro)/CO (Ile), a type II' β-turn at Asn-Ala$^2$, and three transannular hydrogen bonds at NH (Phe)/CO (Ala$^1$), NH (Ala$^1$)/CO (Phe) and NH (Met)/CO (Phe). At temperatures below 5° C., the amide proton Δδ/Δ$_T$ of Ala$^2$ decreased to <0.4, pointing to a new intramolecular hydrogen bond at NH (Ala$^2$)/CONH$_2$ (Asn) arising from the Asn primary amide.

Evaluation of phakellistatin 5 (2) against the NCI human cancer cell line panel gave the following interesting results. Quadruplicate testing of phakellistatin 5 (2) in the U.S. National Cancer Institute's disease-oriented in vitro primary screen revealed distinctive and reproducible GI$_{50}$ mean graph profiles. The approximate mean panel GI$_{50}$ values were 0.6 μM and 3 μM, for peptides I and 2 respectively. Comparative analyses (not shown) of these characteristic patterns of differential growth inhibition by cyclic peptides 1 and 2 did not reveal any strong correlations between the two, nor to the profiles produced by any of the "standard agents" for which common mechanisms of action are known or implicated.

Phakellistatin 6 (3) separated as a colorless amorphous powder (3.75 mg, 7.5×10$^{-7}$ yield): RE (SILICA GEL) 0.40 n-hexane-dichloromethane-methanol (10:5:1), [α]$_D$–128.8° (C=0.37, CH$_3$OH); FABMS m/z 851 [M+H]+; HRFABMS calcd for C$_{47}$H$_{62}$N$_8$O$_7$; 851.4820, found; m/z 851.4825, 0.5 mmu [M+H]$^+$. From the molecular formula combined with initial results from $^1$H-NMR and APT data and UV absorptions at λ 289, 280, 273 (sh) and 213 nm, phakellistatin 6 appeared to be a peptide with mono-substituted phenyl and indole ring systems. The structure of phakellistatin 6 (3) with HMBC and NOE correlations is shown below.

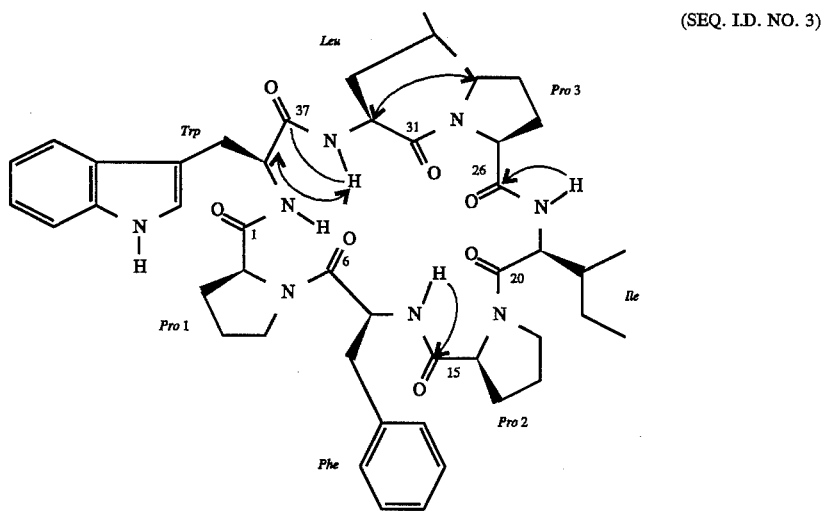

Phakellistatin 6 (3) with HMBC ⟶ and NOE ⟷ Correlations (SEQ. I.D. NO. 3)

Extensive 2D-NMR (COSY, HMQC and HMBC) spectral interpretations resulting from phakellistatin 6 (3) allowed the signal assignments and relationships recorded below in Table 3.

TABLE 3

The High Field (500 MHz) $^1$H- and $^{13}$C-NMR Spectral Assignments for Phakellistatin 6 (3) in CD$_2$Cl$_2$

| | No. | $^{13}$C ppm | $^1$H ppm | J (Hz) | HMBC ($^1$H to $^{13}$C) |
|---|---|---|---|---|---|
| Pro-1 | 1 | 170.88 s | | | |
| | 2 | 62.18 d | 4.16 d | | 1 |
| | 3 | 30.91 t | 1.89 m | | |
| | 4 | 25.94 t | 2.02 m | | |
| | 5 | 46.81 t | 3.42 m | | |
| | | | 3.50 m | | |
| Phe | 6 | 170.54 s | | | |
| | 7 | 53.14 d | 4.67 m | | |
| | 8 | 40.01 t | 2.82 dd | | 6, 7, 9 |
| | | | 3.21 m | | 6, 7, 9 |
| | 9 | 136.27 s | | | |
| | 10 | 129.96 d | 7.11 d | 7.0 | 8, 11 |
| | 11 | 129.03 d | 7.28 dd | 6.5 | 9 |
| | 12 | 127.60 d | 7.24 m | | |
| | 13 | 129.03 d | 7.28 dd | 6.5 | 9 |
| | 14 | 129.96 d | 7.11 d | 7.0 | 8, 13 |
| | NH | | 6.50 d | 4.0 | 15 |
| Pro-2 | 15 | 171.66 s | | | |
| | 16 | 60.69 d | 3.35 d | | |
| | 17 | 31.82 t | 1.86 m | | 15, 16 |
| | | | 1.30 m | | |
| | 18 | 22.38 t | 1.39 m | | 16 |
| | 19 | 47.35 t | 1.49 m | | |
| | | | 3.28 m | | |
| | | | 3.35 m | | |
| Ile | 20 | 169.56 s | | | |
| | 21 | 56.93 d | 4.31 m | | 20 |
| | 22 | 39.41 d | 1.52 m | | 20 |
| | 23 | 26.00 t | 1.37 m | | |
| | | | 1.56 m | | |
| | 24 | 12.15 q | 0.93 t | | 22, 23 |
| | 25 | 14.25 q | 0.87 d | | 22 |
| | NH | | 6.38 d | 6.0 | 26 |
| Pro-3 | 26 | 170.03 s | | | |
| | 27 | 61.34 d | 3.64 d | | |
| | 28 | 29.56 t | 1.87 m | | 26, 27 |
| | 29 | 22.07 t | 1.64 m | | 27 |
| | | | 1.77 m | | |
| | 30 | 47.12 t | 3.65 m | | |
| Leu | 31 | 172.33 s | | | |
| | 32 | 51.20 d | 4.50 m | | 31, 33 |
| | 33 | 39.71 t | 1.43 m | | |
| | | | 1.53 m | | |
| | 34 | 25.70 d | 1.71 m | | 35 |
| | 35 | 20.88 q | 0.92 d | | 33, 34, 36 |
| | 36 | 23.72 q | 1.00 m | | 33, 34, 35 |
| | NH | | 8.20 d | 7.5 | 37 |
| Trp | 37 | 172.65 s | | | |
| | 38 | 54.72 d | 4.67 m | | |
| | 39 | 28.04 t | 3.21 m | | |
| | 40 | 109.82 s | | | |
| | 41 | 124.14 d | 7.21 s | | 40, 42 |
| | NH | | 6.61 brs | | |

TABLE 3-continued

The High Field (500 MHz) $^1$H- and $^{13}$C-NMR Spectral Assignments for Phakellistatin 6 (3) in $CD_2Cl_2$

| No. | $^{13}$C ppm | $^1$H ppm | J (Hz) | HMBC ($^1$H to $^{13}$C) |
|---|---|---|---|---|
| 42 | 127.60 s | | | |
| 43 | 111.73 d | 7.38 d | 7.5 | 42, 44 |
| 44 | 119.93 d | 7.07 t | 7.5 | 42, 43 |
| 45 | 122.67 d | 7.17 t | 7.5 | 46, 47 |
| 46 | 119.24 d | 7.48 d | 7.5 | 45, 47 |
| 47 | 136.66 s | | | |

These corresponded to seven partial structures; namely, isoleucyl, leucyl, phenylalanyl, tryptophanyl and prolyl (x3) units comprising a heptapeptide. Since the molecular formula required 20 unsaturation sites, satisfied in part (19 total) by Pro (x3), Phe, Trp and seven carbonyls, the remaining unsaturation site was attributed to the cyclic peptide ring. Evidence supporting a cyclic peptide structure was also obtained by MS/MS analyses. The HMBC and NOE correlations provided some useful information about the amino acid sequence. HMBC correlations from amide NH protons to amine carbonyl carbon signals such as NH [Leu]($\delta$ 8.20)/CO [Trp]($\delta$ 172.65), NH [Ile]($\delta$ 6.38)/CO [Pro$^3$]($\delta$ 170.33) and NH [Phe]($\delta$ 6.50)/CO [Pro$^2$]($\delta$ 171.66) revealed the presence of Trp-Leu, Pro$^3$-Ile and Pro$^2$-Phe segments. Furthermore, the ROESY spectrum yielded two important NOE correlations between α H [Leu]($\delta$ 4.50) and δ H [Pro$^3$] ($\delta$ 3.65), and NH [Leu]($\delta$ 8.20) and α H [Trp]($\delta$ 4.67) which suggested linking these two segments between Trp-Leu and Pro$^3$-Ile. Because the NH proton of the Trp unit was not observed in the $^1$H-NMR spectra, the connections between NH (Trp) and either CO (Phe) or CO(Pro) could not be ascertained. The uncertainty introduced was resolved by the results of MS/MS mass spectral studies.

The FAB MS/MS analyses revealed internal fragments due to Pro-Trp at m/z 284, Leu/Ile-Pro (or Pro-Leu/Ile) at m/z 211 and Pro-Phe (or Phe-Pro) at m/z 245. These results not only supported the linkages of amino acid units derived by NMR interpretations established, but also the Trp-Pro and Pro-Phe-Pro bonding. Three series of MS fragmentations resulted from protonation of the three prolyl residues followed by ring opening as shown below finally confirmed the sequence of amino acid units of phakellistatin 6 (3) as cyclo-(Pro-Trp-Leu-Pro-Ile-Pro-Phe). SEQ ID. No. 3).

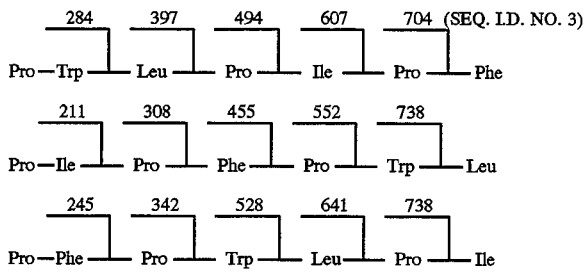

The absolute configuration of the constituent amino acids in peptide 3 was ascertained by analyzing the acid hydrolysate N-pentafluoro-propionyl-isopropyl ester derivatives by means of chiral capillary chromatography (CHIRASIL-Val III column) methods. Based on direct and indirect comparisons, each amino acid unit in phakellistatin 6 (3) was assigned the L-configuration. Due to the presumed decomposition of Trp, its absolute configuration was not assigned.

Phakellistatin 6 was found to display a reassuring level of cancer cell growth inhibition against the murine P388 lymphocytic leukemia ($ED_{50}$ 0.185 μg/ml) and a series human cancer cell lines: ovarian (OVCAR-3; $GI_{50}$ 0.025 μg/ml); CNS (SF-295; $GI_{50}$ 0.041 μg/ml); renal (A498; $GI_{50}$ 0.078 μg/ml); lung (NCI-H460; $GI_{50}$ 0.019 μg/ml); colon (KM20L2; $GI_{50}$ 0.021 μg/ml) and melanoma (SK-MEL-5; $GI_{50}$ 0.032 μg/ml). The consistent presence of proline in this series of cancer cell growth inhibitory cyclic peptides suggests that the three dimensional structures influenced by the cis or trans amide bonding preferences is important.

The isolation and structural elucidation of the cancer cell growth inhibitory cyclic heptapeptide phakellistatins 4–6 from the Western Pacific (Chuuk, Micronesia) marine sponge *Phakellia costata* (class *Demospongia*) is summarized above. When the 1987 collection (500 kg wet wt.) of *P. costata* murine P388 lymphocytic leukemia (PS system) active fractions were examined further for trace PS cell line active components, three cyclic decapeptides were discovered with significant cancer cell growth inhibitory properties.

The bioactive dichloromethane soluble fraction prepared from *P. costata* and used to obtain phakellistatins 4–6 by a solvent partitioning, gel permeation (SEPHADEX LH-20) and partition chromatographic (LH-20) sequence led to a trace PS active fraction that was further separated (PS bioassay). Continued column chromatographic (partition solvent system) separations on SEPHADEX LH-20 and final separation by reversed phase HPLC (PHENOMENEX C8 column and elution with $CH_3CN$–$CH_3OH$–$H_2O$, 10:10:13) afforded phakellistatin 7 (4, 6.5 mg, $1.3 \times 10^{-6}$%), 8 (5, 69.8 mg, $1.4 \times 10^{-5}$%) and 9 ($\delta$, 7.2 mg, $1.4 \times 10^{-6}$%).

Phakellistatin 7 (4), colorless amorphous powder, mp 192°–195° C., $[\alpha]_D$ –106° (C=0.22, $CH_3OH$), exhibited a molecular ion peak in the HRFABMS spectrum at m/z 1109.6401 $[M+H]^+$ corresponding to molecular formula $C_{59}H_{84}N_{10}O_{11}$ (Δ +0.1 mmu). Although interpretation of the high field (500 MHz) $^1$H-NMR spectra from phakellistatin 7 showed only one conformational form in deuteromethanol solution, in deuterochloroform or deuteroacetonitrile at ambient temperatures a complex mixture of conformers was observed. Interpretation of the high-field (500 MHz) 2D-NMR spectra (COSY, HMQC and HMBC) of phakellistatin 7 (4) indicated the presence of four Pro, two Ile, and one each of Leu, Phe, Tyr and Ala units (See: Table 4 below).

TABLE 4

The $^1$H- and $^{13}$C-NMR Spectral Assignments for Phakellistatin 7 in $CD_3OD$ or $CD_3OH$

| | No. | $^{13}$C ppm | $^1$H ppm | HMBC (H to C) | NOE |
|---|---|---|---|---|---|
| Ile-1 | 1 | 172.85 s | | | |
| | 2 | 58.03 d | 4.24 m | | Phe—NH |
| | 3 | 34.06 d | 2.14 m | | |
| | 4 | 26.04 t | 1.49 m | 5, 6 | |
| | | | 1.18 m | 5, 6 | |
| | 5 | 10.23 q | 0.83 t | 3, 6 | |
| | 6 | 17.28 q | 0.91 d | 2, 3, 4 | |
| | NH | | 8.73 brs | | 9 |
| Pro-1 | 7 | 173.64 s | | | |
| | 8 | 62.80 d | 4.32 m | 7, 9, 11 | 13 |
| | 9 | 32.52 t | 2.24 m | 7, 8, 10 | Ile 1-NH |
| | | | 2.50 m | 10, 11 | |
| | 10 | 23.24 t | 1.70 m | | |
| | | | 1.97 m | | |
| | 11 | 48.07 t | 3.52 m | | |
| | | | 3.65 m | | |
| Pro-2 | 12 | 173.32 s | | | |
| | 13 | 60.67 d | 3.68 m | | 8 |
| | 14 | 29.11 t | 1.82 m | 12 | |
| | | | 2.24 m | | |
| | 15 | 26.46 t | 1.83 m | | |

TABLE 4-continued

The $^1$H- and $^{13}$C-NMR Spectral Assignments for Phakellistatin 7 in CD$_3$OD or CD$_3$OH

| | No. | $^{13}$C ppm | $^1$H ppm | HMBC (H to C) | NOE |
|---|---|---|---|---|---|
| | | | 2.14 m | | |
| | 16 | 49.21 t | 3.66 m | | 18 |
| | | | 3.95 m | | 18 |
| Ile-2 | 17 | 171.98 s | | | |
| | 18 | 56.07 d | 4.54 m | 17, 20 | |
| | 19 | 39.70 d | 1.68 m | 21, 22 | |
| | 20 | 25.61 t | 1.69 m | | |
| | | | 1.08 m | | |
| | 21 | 11.11 q | 0.88 t | 19 | |
| | 22 | 15.18 q | 1.02 d | 18, 19 | |
| | NH | | 6.99 brs | | 24 |
| Tyr | 23 | 172.85 s | | | |
| | 24 | 57.64 d | 4.45 m | 23, 25 | Ile 2-NH |
| | 25 | 33.40 t | 3.42 m | | |
| | | | 3.13 m | 24, 26 | |
| | 26 | 130.44 s | | | |
| | 27 | 132.15 d | 6.97 d | 25, 28 | |
| | 28 | 115.64 d | 6.52 d | 26, 29 | |
| | 29 | 115.80 s | | | |
| | 30 | 115.64 d | 6.52 d | 26, 29 | |
| | 31 | 132.15 d | 6.97 d | 25, 30 | |
| | OH | | 9.02 brs | | |
| | NH | | 9.23 brs | | 33 |
| Pro-3 | 32 | 172.85 s | | | |
| | 33 | 62.47 d | 4.20 m | 32, 34 | 38 |
| | 34 | 31.86 t | 2.48 m | 36 | |
| | | | 2.05 m | 33, 35 | |
| | 35 | 23.35 t | 1.70 m | | |
| | | | 1.97 m | | |
| | 36 | 47.99 t | 3.51 m | | |
| | | | 3.53 m | | |
| Pro-4 | 37 | 172.47 s | | | |
| | 38 | 59.98 d | 3.24 m | | 33 |
| | 39 | 29.79 t | 1.60 m | | |
| | | | 2.08 m | 37 | |
| | 40 | 25.61 t | 1.80 m | | |
| | | | 1.10 m | | |
| | 41 | 47.79 t | 3.44 m | | |
| | | | 3.62 m | | |
| Lue | 42 | 170.72 s | | | |
| | 43 | 49.97 d | 4.66 m | 42, 44 | 41 |
| | 44 | 42.91 t | 1.22 m | 43 | |
| | | | 1.49 m | | |
| | 45 | 25.74 d | 1.58 m | | |
| | 46 | 21.96 q | 1.01 d | 44, 45 | |
| | 47 | 23.98 q | 0.87 d | 45, 46 | |
| | NH | | 7.01 brs | | 49 |
| Ala | 48 | 174.14 s | | | |
| | 49 | 50.96 d | 4.55 m | 48, 50 | Lue—NH |
| | 50 | 18.06 q | 1.36 d | 48, 49 | Ala—NH |
| | NH | | 8.08 brs | | 50, 52 |
| Phe | 51 | 174.53 s | | | |
| | 52 | 58.03 d | 4.22 m | | Ala—NH |
| | 53 | 39.02 t | 2.84 dd | 51, 52 | |
| | | | 3.06 dd | 51, 54 | |
| | 54 | 137.53 s | | | |
| | 55 | 130.81 d | 7.24 d | 53, 57 | |
| | 56 | 129.96 d | 7.34 d | 54 | |
| | 57 | 128.32 d | 7.30 m | 55 | |
| | 58 | 129.32 d | 7.34 d | 54 | |
| | 59 | 130.81 d | 7.24 m | 53, 57 | |
| | NH | | 7.08 brs | | 2 |

The cyclodecapeptide sequence of amino acid units was established as cyclo-(Pro-Pro-Ile-Phe-Ala-Leu-Pro-Pro-Tyr-Ile) (SEQ. I.D. No. 4) by tandem mass spectral studies. Protonation of the four proline residues by FAB mass spectrometry produced four series of fragmentations which were interpreted by MS/MS methods and are shown below.

| m/z: | | 195 | 308 | 455 | 526 | 639 | 736 | 833 | 996 | | |
|---|---|---|---|---|---|---|---|---|---|---|---|
| | Pro | Pro | Ile | Phe | Ala | Leu | Pro | Pro | Tyr | Ile | (SEQ. I.D. NO.) |
| m/z: | | 211 | 358 | 429 | 542 | 639 | 736 | 899 | 1012 | | |
| | Pro | Ile | Phe | Ala | Leu | Pro | Pro | Tyr | Ile | Pro | |
| m/z: | | 195 | 358 | 471 | 568 | 665 | 778 | 925 | 996 | | |
| | Pro | Pro | Tyr | Ile | Pro | Pro | Ile | Phe | Ala | Leu | |
| m/z: | | 261 | 374 | 471 | 568 | 681 | 828 | 899 | 1012 | | |
| | Pro | Tyr | Ile | Pro | Pro | Ile | Phe | Ala | Leu | Pro | |

The amino acid sequence of decapeptide 4 was further substantiated by the following NOE correlations (in CD$_3$OH): NH(Phe)/αH(Ile$^1$), NH(Ile$^1$)/βH(Pro$^1$), αH(Pro$^1$)/αH(Pro$^2$), δH(Pro$^2$)/αH(Ile$^2$), NH(Ile$^2$)/αH(Tyr), NH(Tyr)/αH(Pro$^3$), αH(Pro$^3$)/αH(Pro$^4$), δH(Pro$^4$)/αH(Leu), NH(Leu)/αH(Ala) and NH(Ala)/αH(Phe). Thus, structure 4, as shown below, was assigned to phakellistatin 7.

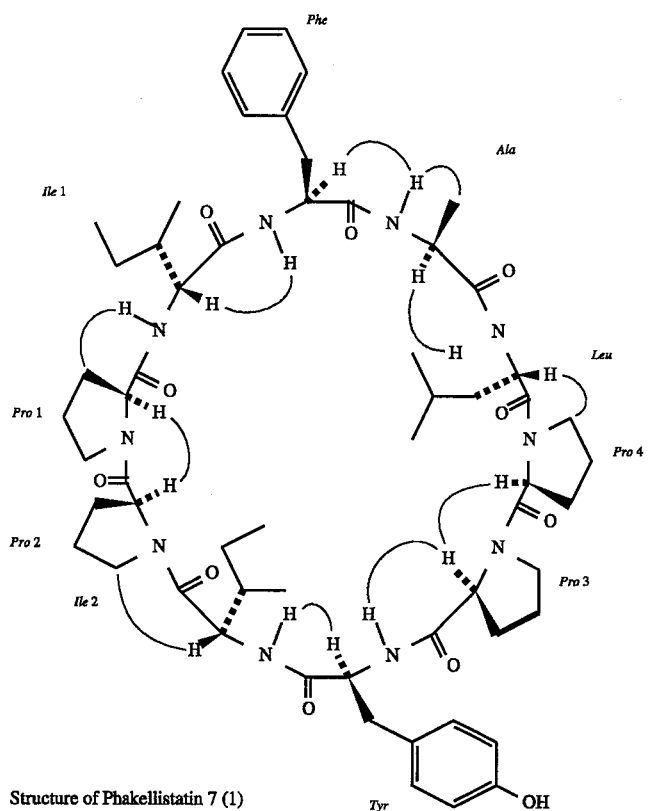

Structure of Phakellistatin 7 (1) and NOE correlations

Phakellistatin 8 (5), colorless crystals from methanol-water, mp 188°–191° C., $[\alpha]_D$ 112°–5° (c=0.16, CH$_3$OH), exhibited a HRFABMS molecular ion peak at m/z 1137.6714 [M+H]$^+$ leading to molecular formula C$_{61}$H$_{88}$N$_{10}$O$_{11}$ (Δ+0.1 mmu). Peptide 5 appeared essentially as one conformer in deuteriochloroform. The presence of Pro, Ile, Leu, Val, Phe and Tyr units in a ratio 4:2:1:1:1:1 was confirmed by detailed analyses of 2D-NMR spectra (COSY, HMQC and HMBC, See: Table 5).

TABLE 5

The $^1$H- and $^{13}$C-NMR Spectral Assignments for Phakellistatin 8 in CDCl$_3$

| | No. | $^{13}$C ppm | $^1$H ppm | HMBC (H to C) | NOE |
|---|---|---|---|---|---|
| Ile-1 | 1 | 173.91 s | | | |
| | 2 | 58.27 d | 4.24 m | 1 | Phe—NH |
| | 3 | 34.11 d | 2.05 m | | |
| | 4 | 25.26 d | 1.17 m | 3, 5, 6 | |
| | | | 1.40 m | | |
| | 5 | 9.84 q | 0.82 t | 3, 4 | |
| | 6 | 16.13 q | 0.93 d | 2, 3, 4 | |
| | NH | | 8.07 d | | 9 |
| Pro-1 | 7 | 171.44 s | | | |
| | 8 | 61.25 d | 4.02 m | 7 | |
| | 9 | 30.27 t | 1.92 m | 8, 10 | 13 |
| | | | 2.67 m | | |
| | 10 | 22.08 t | 1.70 m | | Ile 1-NH |
| | | | 1.90 m | | |
| | 11 | 46.19 t | 3.36 m | 9, 10 | |
| | | | 3.48 m | 9 | |
| Pro-2 | 12 | 171.24 s | | | |
| | 13 | 58.66 d | 3.30 m | 12 | 9 |
| | 14 | 28.23 t | 1.68 m | | |
| | 15 | 25.26 t | 2.01 m | | |
| | | | 1.82 m | | |
| | | | 2.07 m | | |
| | 16 | 47.94 t | 3.86 m | 14, 15 | 18 |
| | | | 3.61 m | 14, 15 | 18 |
| Ile-2 | 17 | 173.57 s | | | |
| | 18 | 54.99 d | 4.63 m | 19, 22 | 16 |
| | 19 | 37.01 d | 1.80 m | | |
| | 20 | 23.67 t | 1.53 m | 18, 19 | |
| | 21 | 11.08 q | 0.86 m | 19, 20 | |
| | 22 | 15.23 q | 1.03 d | | |
| | NH | | 6.95 d | | |
| Tyr | 23 | 171.44 s | | | |
| | 24 | 57.51 d | 4.13 m | 23 | |
| | 25 | 31.50 t | 3.32 m | | |
| | | | 3.50 m | | |
| | 26 | 130.14 s | | | |
| | 27 | 130.75 d | 7.09 d | 26, 28 | |
| | 28 | 114.54 d | 6.64 d | | |
| | 29 | 154.84 s | | | |
| | 30 | 114.54 d | 6.64 d | | |
| | 31 | 130.75 d | 7.09 d | 26, 29 | |
| | OH | | 9.18 d | | |
| | NH | | 8.49 d | | 33 |
| Pro-3 | 32 | 170.24 s | | | |
| | 33 | 58.25 d | 3.17 m | 32 | Tyr—NH, 38 |
| | 34 | 31.23 t | 2.54 m | 35, 36 | |
| | | | 2.12 m | 35, 36 | |
| | 35 | 21.98 t | 1.70 m | | |
| | | | 1.91 m | | |

TABLE 5-continued

The $^1$H- and $^{13}$C-NMR Spectral Assignments for Phakellistatin 8 in CDCl$_3$

|  | No. | $^{13}$C ppm | $^1$H ppm | HMBC (H to C) | NOE |
|---|---|---|---|---|---|
|  | 36 | 46.65 t | 3.49 m |  |  |
|  |  |  | 3.40 m |  |  |
| Pro-4 | 37 | 171.14 s |  |  |  |
|  | 38 | 61.00 d | 4.07 m | 37 | 33 |
|  | 39 | 28.93 t | 1.68 m |  |  |
|  |  |  | 1.90 m |  |  |
|  | 40 | 24.88 t | 2.02 m | 38, 41 |  |
|  | 41 | 46.94 t | 3.46 m |  |  |
|  |  |  | 3.71 m |  | 43 |
| Lue | 42 | 169.95 s |  |  |  |
|  | 43 | 48.40 d | 4.77 m | 42 | 41 |
|  | 44 | 41.29 t | 1.30 m |  |  |
|  | 45 | 24.65 d | 1.51 m |  |  |
|  | 46 | 21.11 q | 0.99 d | 44, 45 |  |
|  | 47 | 23.50 q | 0.88 d | 45, 46 |  |
|  | NH |  | 6.95 d |  | 49 |
| Val | 48 | 171.34 s |  |  |  |
|  | 49 | 59.14 d | 4.54 d | 48 | Leu—NH |
|  | 50 | 29.60 d | 2.58 m |  |  |
|  | 51 | 19.56 q | 0.93 d |  |  |
|  | 52 | 16.13 q | 0.93 d | 49, 50 |  |
|  | NH |  | 7.69 d |  |  |
| Phe | 53 | 172.76 s |  |  |  |
|  | 54 | 60.06 d | 4.00 m |  |  |
|  | 55 | 36.64 t | 2.80 m |  |  |
|  |  |  | 3.45 m | 53, 56 |  |
|  | 56 | 138.94 s |  |  |  |
|  | 57 | 129.77 d | 7.22 m | 56 |  |
|  | 58 | 128.54 d | 7.29 dd | 59 |  |
|  | 59 | 126.67 d | 7.25 dd |  |  |
|  | 60 | 128.54 d | 7.29 dd | 59 |  |
|  | 61 | 129.77 d | 7.22 m | 56 |  |
|  | NH |  | 7.15 d |  | 2 |

The ROESY spectrum of decapeptide 5 provided NOE correlations between NH(Phe)/αH(Ile$^1$), NH(Ile$^1$)/αH (Pro$^1$), αH(Pro$^2$)/αH(Pro$^2$), δH(Pro$^2$)/αH(Ile$^2$), NH(Tyr)/αH(Pro$^3$), αH(Pro$^3$)/αH(Pro$^4$), δH(Pro$^4$)/αH(neu) and NH(Leu)/αH(Val), which inferred the presence of Ile-Pro-Pro-Ile-Phe and Val-Leu-Pro-Pro-Tyr segments. Unsaturation calculations for the molecular formula pointed to a cyclic peptide. While the complete peptide sequence was not unequivocally solved using the available NMR data, the MS/MS analysis shown below did provide additional sequence information and led to the cyclo-(Pro-Pro-Ile-Phe-Val-Leu-Pro-Pro-Tyr-Ile) (SEQ. I.D. No. 5) structural assignment for phakellistatin 8 (5) as shown below with NOE correlations.

| m/z: |  | 195 | 308 | 455 | 554 | 667 | 764 | 861 | 1024 |  | SEQ. I.D. NO.9 |
|---|---|---|---|---|---|---|---|---|---|---|---|
|  | Pro | Pro | Ile | Phe | Val | Leu | Pro | Pro | Tyr | Ile |  |
| m/z: |  | 211 | 358 | 457 | 570 | 667 | 764 | 927 | 1040 |  |  |
|  | Pro | Ile | Phe | Val | Leu | Pro | Pro | Tyr | Ile | Pro |  |
| m/z: |  | 195 | 358 | 471 | 568 | 665 | 778 | 925 | 1024 |  |  |
|  | Pro | Pro | Tyr | Ile | Pro | Pro | Ile | Phe | Val | Leu |  |
| m/z: |  | 261 | 374 | 471 | 568 | 681 | 828 | 927 | 1040 |  |  |
|  | Pro | Tyr | Ile | Pro | Pro | Ile | Phe | Val | Leu | Pro |  |

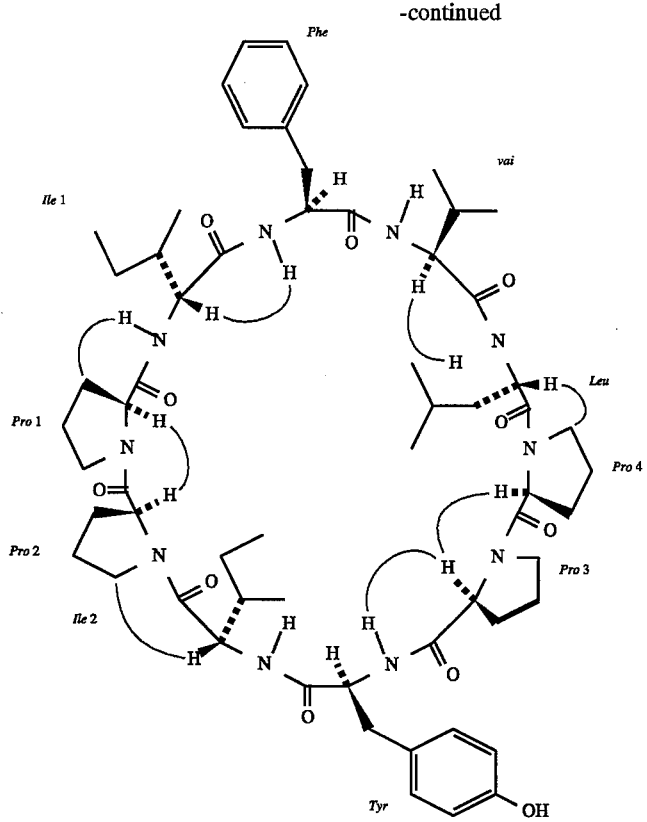

Structure of Phakellistatin 8 (2)
and NOE correlations

Phakellistatin 9 (6), colorless amorphous powder mp 184°–188° C., $[\alpha]_D$–113° (C=0.68, $CH_3OH$), exhibited a pseudomolecular ion peak in the FAB-MS at m/z 1123. The molecular formula was determined to be $C_{60}H_{86}N_{10}O_{11}$ by HRFABMS (m/z 1123.6553 $[M+H]^+$, Δ-0.2 mmu). Peptide 6 also appeared as one conformer in deuteromethanol, but not deuterochloroform or deuteroacetonitrile. The high field (500 MHz) $^1H$-NMR and APT data in combination with results of extensive COSY, HMQC and HMBC experiments provided evidence that phakellistatin 9 was another decapeptide comprised of Pro(x4), Val(x2), Ile, Leu, Phe and Tyr and are shown in Table 6, below.

TABLE 6

The $^1H$- and $^{13}C$-NMR Spectral Assignments for Phakellistatin 9 in $CD_3OD$ or $CD_3OH$

|  | No. | $^{13}C$ ppm | $^1H$ ppm | HMBC (H to C) | NOE |
|---|---|---|---|---|---|
| Ile | 1 | 173.83 s * |  |  |  |
|  | 2 | 60.36 d | 4.19 m |  |  |
|  | 3 | 35.58 d | 2.05 m |  |  |
|  | 4 | 26.34 d | 1.13 m | 3, 5, 6 |  |
|  |  |  | 1.46 m |  |  |
|  | 5 | 10.37 q | 0.84 t | 3, 4 |  |
|  | 6 | 17.02 q | 0.87 d |  |  |
|  | NH |  | 8.39 brs |  |  |
| Pro-1 | 7 | 172.75 s * |  |  |  |
|  | 8 | 62.42 d | 4.17 m | 9, 10, 11 | 13 |
|  | 9 | 31.45 t | 2.01 m | 8 |  |
|  |  |  | 2.45 m | 10, 11 |  |
|  | 10 | 23.24 t | 1.66 m |  |  |
|  |  |  | 1.98 m |  |  |
|  | 11 | 47.89 t | 3.40 m |  |  |

TABLE 6-continued

The $^1H$- and $^{13}C$-NMR Spectral Assignments for Phakellistatin 9 in $CD_3OD$ or $CD_3OH$

|  | No. | $^{13}C$ ppm | $^1H$ ppm | HMBC (H to C) | NOE |
|---|---|---|---|---|---|
|  |  |  | 3.46 m |  |  |
| Pro-2 | 12 | 172.50 s * |  |  |  |
|  | 13 | 60.36 d | 4.10 m | 12 | 8 |
|  | 14 | 29.57 t | 1.74 m |  |  |
|  |  |  | 2.17 m |  |  |
|  | 15 | 26.26 t | 1.86 m |  |  |
|  |  |  | 1.48 m |  |  |
|  | 16 | 49.20 t | 3.78 m |  | 18 |
|  |  |  | 3.61 m |  | 18 |
| Val-1 | 17 | 173.45 s * |  |  |  |
|  | 18 | 56.94 d | 4.54 m | 19, 20, 21 | 16 |
|  | 19 | 32.50 d | 2.03 m |  |  |
|  | 20 | 18.35 q | 0.89 d | 18, 19, 21 |  |
|  | 21 | 19.95 q | 1.02 m | 18, 19, 20 |  |
|  | NH |  | 7.20 brs |  |  |
| Tyr | 22 | 172.85 s * |  |  |  |
|  | 23 | 57.65 d | 4.34 dd |  |  |
|  | 24 | 33.60 t | 3.09 m |  |  |
|  |  |  | 3.35 m |  |  |
|  | 25 | 130.24 s |  |  |  |
|  | 26 | 132.04 d | 6.99 d | 23, 27, 28 |  |
|  | 27 | 115.79 d | 6.55 d | 25, 28 |  |
|  | 28 | 156.89 s |  |  |  |
|  | 29 | 115.79 d | 6.55 d | 25, 28 |  |
|  | 30 | 132.04 d | 6.99 d | 23, 28, 29 |  |
|  | NH |  | 9.05 brs |  |  |
| Pro-3 | 31 | 171.93 s * |  |  |  |
|  | 32 | 62.70 d | 4.20 m | 34 | 37 |
|  | 33 | 32.29 t | 2.45 m | 34, 35 |  |

TABLE 6-continued

The $^1$H- and $^{13}$C-NMR Spectral Assignments for Phakellistatin 9 in $CD_3OD$ or $CD_3OH$

| | No. | $^{13}$C ppm | $^1$H ppm | HMBC (H to C) | NOE |
|---|---|---|---|---|---|
| | | | 2.17 m | 32 | |
| | 34 | 23.09 t | 1.66 m | | |
| | | | 1.90 m | | |
| | 35 | 47.79 t | 3.46 m | | |
| | | | 3.40 m | | |
| Pro-4 | 36 | 172.75 s * | | | |
| | 37 | 59.96 d | 4.22 m | | 32 |
| | 38 | 29.15 t | 1.61 m | | |
| | | | 2.05 m | | |
| | 39 | 26.00 t | 2.02 m | | |
| | 40 | 48.36 t | 3.48 m | | 42 |
| | | | 3.67 m | | 42 |
| Lue | 41 | 171.21 s * | | | |
| | 42 | 49.98 d | 4.75 m | | 40 |
| | 43 | 42.41 t | 1.33 m | | |
| | | | 1.44 m | | |
| | 44 | 25.96 d | 2.00 m | | |
| | 45 | 21.43 q | 1.03 d | 43, 44, 46 | |
| | 46 | 23.93 q | 0.91 d | 43, 44, 45 | |
| | NH | | 6.96 brs | | |
| Val-2 | 47 | 172.73 s * | | | |
| | 48 | 60.79 d | 4.49 d | 49, 50, 51 | |
| | 49 | 30.97 d | 2.50 d | | |
| | 50 | 17.12 q | 1.01 d | 48, 49 | |
| | 51 | 19.76 q | 0.89 q | 49 | |
| | NH | | 7.89 brs | | |
| Phe | 52 | 172.85 s * | | | |
| | 53 | 59.96 d | 4.17 m | | |
| | 54 | 38.69 t | 2.91 m | 55, 56, 60 | |
| | | | 3.20 m | 55, 56, 60 | |
| | 55 | 138.40 s | | | |
| | 56 | 130.81 d | 7.22 m | 54, 58 | |
| | 57 | 129.82 d | 7.33 m | 55 | |
| | 58 | 128.08 d | 7.32 m | 56, 60 | |
| | 59 | 129.82 d | 7.33 m | 55 | |
| | 60 | 130.81 d | 7.22 m | 54, 58 | |
| | NH | | 7.49 d | | |

* These carbonyl carbon chemical shift data could be exchanged.

NOE correlations were found between αH (Pro$^1$)/all (Pro$^2$), αH(Val$^1$)/αH(Pro$^2$), αH(Pro4)/αH(Pro$^4$) and αH(Leu)/δH(Pro4). The structure and NOE correlations are shown below:

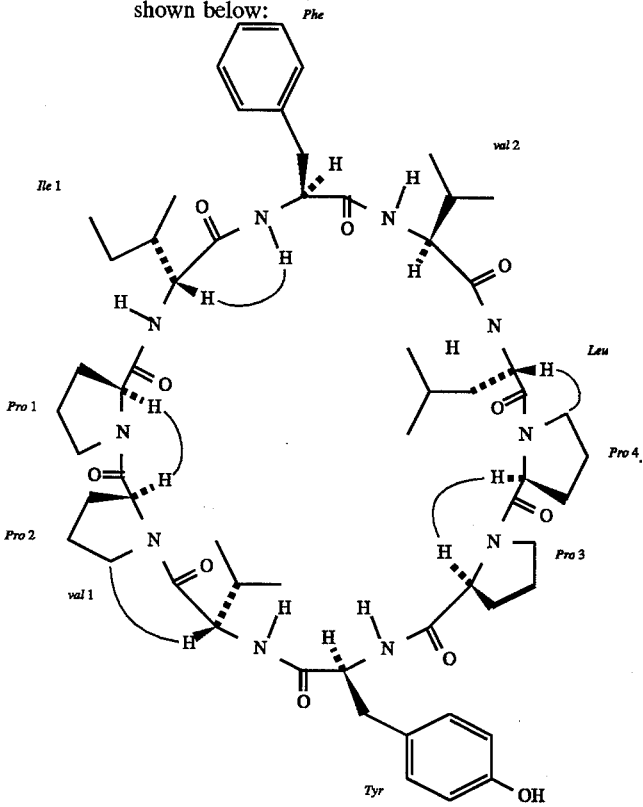

Structure of Phakellistatin 9 (3) and NOE correlations

A tandem MS/MS study of peptide 6 gave definitive sequence information. Results of four series of FABMS fragmentations arising from protonation of the four Pro units were indicative of a cyclic peptide structure and are shown below.

| m/z: | | 195 | 308 | 455 | 554 | 667 | 764 | 861 | 1024 | | |
|---|---|---|---|---|---|---|---|---|---|---|---|
| | Pro | Pro | Ile | Phe | Val | Leu | Pro | Pro | Tyr | Val | (SEQ. I.D. NO.) |
| m/z: | | | 211 | 358 | 457 | 570 | 667 | 764 | 927 | 1026 | |
| | Pro | Ile | Phe | Val | Leu | Pro | Pro | Tyr | Val | Pro | |
| m/z: | | 195 | 358 | 457 | 554 | 651 | 764 | 911 | 1010 | | |
| | Pro | Pro | Tyr | Val | Pro | Pro | Ile | Phe | Val | Leu | |
| m/z: | | | 261 | 360 | 457 | 554 | 667 | 814 | 913 | 1026 | |
| | Pro | Tyr | Val | Pro | Pro | Ile | Phe | Val | Leu | Pro | |

Other internal fragment ions corresponded to the following segments [M+H-Pro-Pro-Ile]$^+$ at m/z 816, [M+H-Pro-Ile-Phe]$^+$ at m/z 766 and [M+H-Pro-Ile-Phe-Val]$^+$ at m/z 570. Further analysis of the MS/MS and NMR data completed the structural elucidation of phakellistatin 9 (6) as cyclo-(Pro-Pro-Ile-Phe-Val-Leu-Pro-Pro-Tyr-Val) (SEQ. I.D. No. 6).

The chirality of the amino acid units of phakellistatins 7 (4), 8 (5) and 9 (6) were determined by GC analysis of N-pentafluoropropyl isopropyl ester derivatives of the respective propionic acid-hydrochloric acid hydrolysates. All of the amino acids proved to have the (S)-configuration. Furthermore, cross peaks for αH(Pro$_1$)/αH(Pro$^2$) and αH(Pro$_3$)/αH(Pro$^4$) were observed in all ROESY spectra recorded for phakellistatins 7 (4), 8 (5) and 9 (6) indicating all have cis-amide bonds at CO(Pro$^2$)/NH(Pro$^1$) and CO(Pro$^4$)/NH(Pro$^3$). Additional evidence supporting the cis geometries were obtained by the $^{13}$C chemical shifts differences (Δδβγ 8.19–9.28 ppm) of the β and γ carbons of Pro$^1$ and Pro$^3$ units (Tables 4, 5 and 6).

Interestingly, phakellistatins 7 (4), 8 (5) and 9 (6) obtained from the same source are not only structurally similar, but they also display quite comparable cytotoxicities against the P388 cell lines in vitro (ED$_{50}$ 3.0, 4.1 and 2.9 μg/ml respectively).

From the foregoing, it is readily apparent that a useful embodiment of the present invention has been herein described and illustrated which fulfills all of the aforestated objectives in a remarkably unexpected fashion. It is, of course, understood that such modifications, alterations and adaptations as may readily occur to the artisan confronted with this disclosure are intended within the spirit of this disclosure which is limited only by the scope of the claims appended hereto.

Accordingly, what is claimed is:

1. A cyclic peptide selected from the group consisting of phakellistatin 4, phakellistatin 5, phakellistatin 6, phakellistatin 7, phakellistatin 8, and phakellistatin 9.

2. A cyclic peptide according to claim 1, wherein the cyclic peptide is designated phakellistatin 4 and has the structure cyclo-(Pro-Thr-Pro-Phe-Ile-Phe-Ser) (SEQ. I.D. NO. 1).

3. A cyclic peptide according to claim 1, wherein the cyclic peptide is designated phakellistatin 5 and has the structure cyclo-(Pro-Phe-Asn-Ala-Met-Ala-Ile) (SEQ. I.D. NO. 2).

4. A cyclic peptide according to claim 1, wherein the cyclic peptide is designated phakellistatin 6 and has the structure cyclo-(Pro-Trp-Leu-Pro-Ile-Pro-Phe) (SEQ. I.D. NO. 3).

5. A cyclic peptide according to claim 1, wherein the cyclic peptide is designated phakellistatin 7 and has the structure cyclo-(Pro-Pro-Ile-Phe-Ala-Leu-Pro-Pro-Tyr-Ile) (SEQ. I.D. NO. 4).

6. A cyclic peptide according to claim 1, wherein the cyclic peptide is designated phakellistatin 8 and has the structure cyclo-(Pro-Pro-Ile-Phe-Val-Leu-Pro-Pro-Tyr-Ile) (SEQ. I.D. NO. 5).

7. A cyclic peptide according to claim 1, wherein the cyclic peptide is designated phakellistatin 9 and has the structure cyclo-(Pro-Pro-Ile-Phe-Val-Leu-Pro-Pro-Tyr-Val) (SEQ. I.D. NO. 6).

8. A cyclic heptapeptide selected from the group consisting of cyclo-(Pro-Thr-Pro-Phe-Ile-Phe-Ser), (SEQ. I.D. NO. 1), cyclo-(Pro-Phe-Asn-Ala-Met-Ala-Ile), (SEQ. I.D. NO. 2), and cyclo-(Pro-Trp-Leu-Pro-Ile-Pro-Phe) (SEQ. I.D. NO. 3).

9. A cyclic heptapeptide according to claim 8 designated herein as phakellistatin 4 and has the structural formula cyclo-(Pro-Thr-Pro-Phe-Ile-Phe-Ser) (SEQ. I.D. NO. 1).

10. A cyclic heptapeptide according to claim 8 designated herein as phakellistatin 5 and has the structural formula cyclo-(Pro-Trp-Leu-Pro-Ile-Pro-Phe) (SEQ. I.D. NO. 3).

11. A cyclic decapeptide wherein amino acid units 1–4 are Pro-Pro-Ile-Phe, units 6–9 are Leu-Pro-Pro-Tyr, unit 5 is selected from the group consisting of Ala and Val, and unit 10 is selected from the group consisting of Ile and Val (SEQ. I.D. NO. 4, 5 & 6).

12. A cyclic decapeptide according to claim 11 wherein unit 5 is Ala, unit 10 is Ile and said decapeptide is designated herein as phakellistatin 7.

13. A cyclic decapeptide according to claim 11 wherein unit 5 is Val, unit 10 is Ile and said decapeptide is designated herein as phakellistatin 8.

14. A cyclic decapeptide according to claim 11 wherein unit 5 is Val, unit 10 is Val and said decapeptide is designated herein as phakellistatin 9.

* * * * *